(12) United States Patent
Vandenabeele et al.

(10) Patent No.: US 9,862,678 B2
(45) Date of Patent: Jan. 9, 2018

(54) 3,4-DIAMINOBENZENESULFONAMIDE DERIVATIVES FOR INHIBITING CELL DEATH

(71) Applicants: VIB VZW, Ghent (BE); Universiteit Gent, Ghent (BE); Universiteit Antwerpen, Antwerp (BE)

(72) Inventors: Peter Vandenabeele, Sint-Amandsberg (BE); Tom Vanden Berghe, Haasdonk (BE); Koen Augustyns, Hoogstraten (BE); Jurgen Joossens, Zoersel (BE); Pieter Van Der Veken, Sint-Katelijne-Waver (BE); Sam Hofmans, Willebroek (BE)

(73) Assignees: VIB VZW, Ghent (BE); Universiteit Gent, Ghent (BE); Universiteit Antwerpen, Antwerp (BE)

( * ) Notice: Subject to any disclaimer, the term of this patent is extended or adjusted under 35 U.S.C. 154(b) by 0 days.

(21) Appl. No.: 15/525,480

(22) PCT Filed: Nov. 16, 2015

(86) PCT No.: PCT/EP2015/076680
§ 371 (c)(1),
(2) Date: May 9, 2017

(87) PCT Pub. No.: WO2016/075330
PCT Pub. Date: May 19, 2016

(65) Prior Publication Data
US 2017/0313653 A1 Nov. 2, 2017

(30) Foreign Application Priority Data

Nov. 14, 2014 (GB) .................................. 1420235.2

(51) Int. Cl.
*C07C 311/39* (2006.01)
*C07C 311/40* (2006.01)
*C07D 295/26* (2006.01)
*C07D 213/38* (2006.01)
*C07D 239/26* (2006.01)

(52) U.S. Cl.
CPC .......... *C07C 311/39* (2013.01); *C07C 311/40* (2013.01); *C07D 213/38* (2013.01); *C07D 239/26* (2013.01); *C07D 295/26* (2013.01); *C07C 2601/02* (2017.05); *C07C 2601/08* (2017.05); *C07C 2601/14* (2017.05); *C07C 2601/18* (2017.05); *C07C 2602/42* (2017.05); *C07C 2603/74* (2017.05)

(58) Field of Classification Search
CPC ..................................................... C07C 311/39
See application file for complete search history.

(56) References Cited

U.S. PATENT DOCUMENTS

| 5,011,472 A | 4/1991 | Aebischer et al. |
| 5,023,252 A | 6/1991 | Hseih |

FOREIGN PATENT DOCUMENTS

| WO | 2013152039 A1 | 10/2013 |
| WO | 2016075330 | 5/2016 |

OTHER PUBLICATIONS

Hayman, 1964, J. Pharm. Pharmacol, VOl. 16, p. 677-689.*
Dixon et al., Ferroptosis: An Iron-Dependent Form of Non-Apoptotic Cell Death, Cell, May 25, 2013, pp. 1060-1072, vol. 149, No. 5.
PCT International Search Report dated Jan. 12, 2016, dated Jan. 20, 2016, PCT/EP2015/076680, 4 pages.
PCT Written Opinion of the International Searching Authority dated Jan. 12, 2016, dated Jan. 20, 2016, PCT/EP2015/076680, 6 pages.

* cited by examiner

*Primary Examiner* — Rebecca Anderson
*Assistant Examiner* — Karen Cheng
(74) *Attorney, Agent, or Firm* — TraskBritt, P.C.

(57) ABSTRACT

This disclosure relates to a novel class of compounds having the structure of formula I as defined herein and pharmaceutical compositions comprising a compound of formula I or a pharmaceutically acceptable salt thereof. This disclosure also comprises methods of treating a subject by administering a therapeutically effective amount of a compound of formula I or a pharmaceutically acceptable salt thereof to the subject. These compounds are useful for the conditions disclosed herein. This disclosure further comprises methods for making the compounds of formula I and corresponding intermediates.

9 Claims, No Drawings

3,4-DIAMINOBENZENESULFONAMIDE DERIVATIVES FOR INHIBITING CELL DEATH

CROSS-REFERENCE TO RELATED APPLICATIONS

This application is a national phase entry under 35 U.S.C. §371 of International Patent Application PCT/EP2015/076680, filed Nov. 16, 2015, designating the United States of America and published in English as International Patent Publication WO 2016/075330 A1 on May 16, 2016, which claims the benefit under Article 8 of the Patent Cooperation Treaty to Great Britain Patent Application Serial No. 1420235.2, filed Nov. 14, 2014.

TECHNICAL FIELD

This application relates to the field of cell death, in particular regulated necrosis, more particularly iron dependent cell death. The disclosure provides compounds useful for inhibiting undesired cell death associated with diseases such as neurodegeneration and ischemia—reperfusion injury. The disclosure also provides compositions containing a pharmaceutically acceptable carrier and one or more compounds from the disclosure.

BACKGROUND

Cell death is crucial for normal development, homeostasis, and the prevention of hyperproliferative diseases such as cancer. It was once thought that almost all regulated cell death in mammalian cells resulted from the activation of caspase-dependent apoptosis. Very recently this view has been challenged by the discovery of several regulated non-apoptotic cell death pathways activated in specific disease states. Regulated necrosis is defined as a genetically controlled cell death process that eventually results in cellular leakage, and is morphologically characterized by cytoplasmic granulation, as well as organelle and/or cellular swelling. An overview of these different regulated necrosis pathways is presented in T. Vanden Berghe et al. (2014) *Nat. Rev. Mol. Cell. Biol.* 15:135-147. Ferroptosis is one recognized form of regulated necrosis and its hallmark is the production of iron-dependent reactive oxygen species (ROS). Ferroptosis is partly mediated through inhibiting the system $Xc^-$ Cys/Glu antiporter, which allows the exchange of extracellular L-Cys and intracellular L-Glu across the plasma membrane. Ferroptosis involves metabolic dysfunction that results in the production of both cytosolic and lipid ROS, independent of mitochondria but dependent on NADPH oxidases. It is believed that ROS generated by Fenton-type reactions (dependent on the availability of catalytic ferrous iron), rather than the mitochondrial electron transport chain are the main drivers of ferroptosis. Glutathione (GSH) peroxidase 4 (GPX4) is a crucial inhibitor of ferroptosis, and its activity relies on GSH levels. Therefore, GSH depletion typically leads to loss-of-function of GPX4, resulting in ROS-mediated lipid peroxidation. In addition to ferroptosis, glutamine- and oxidative stress-induced cell death are inhibited by iron chelation. In line with this, iron-dependent neuronal cell death is blocked by metal protein-attenuating compounds (e.g., clioquinol) and iron chelators (e.g., desferroxamine), which are being explored for the treatment of neurodegenerative diseases. Another type of regulated necrosis is oxytosis which is also induced when the $Xc^-$ Cys/Glu antiporter is inhibited through an excess of the neurotransmitter glutamine, the latter process is often designated as excitotoxicity in neuronal cells. Because of the clear mechanistic overlaps between oxytosis and ferroptosis it is not excluded that the use of modulators of ferroptosis in disease will also target the same disease processes which are associated with oxytosis. Disease processes where undesired ferroptosis and/or oxytosis occur are typically disorders where an oxidative stress factor is involved such as, for example, in several neurodegenerative diseases, liver-, cardiac- and kidney-ischemia—reperfusion injury, stroke, sepsis, diabetes and epilepsy. Oxidative stress due to iron overload is, for example, highly relevant in organs accumulating iron such as the brain, kidney and liver. Several compounds have been described in the art which are able to inhibit ferroptosis such as, for example, WO2013/152039, R. Skouta et al. (2014) *J. Am. Chem. Soc.* 136:4551-4556, and A. Linkermann et al. (2014) www.pnas.org/cgi/doi/10.1073/pnas.1415518111). The prior art highlights the importance of the ethyl-ester in the maintenance of the potency of the first-in-class compound ferroptosis inhibitor molecule (designated as Ferrostatin-1) and suggests chain modifications of the ester, see Skouta et al. (2014), for generating improved molecules. Indeed, the latter reference also teaches that esters modified to amides at the same position have a lower EC50. In addition, Linkerman et al. (2014) also disclose that improved pharmacokinetic variants of Ferrostatin-1 should be ester analogs.

SUMMARY OF THE DISCLOSURE

It would be desirable to generate additional compounds which can inhibit or reduce ferroptosis, in particular compounds with an improved physicochemical and/or pharmacokinetic profile. This application has surprisingly found that the ester modification in Ferrostatin-1 analogs towards a sulfonamide resulted in a set of highly potent and improved compounds. These compounds can be used to treat diseases where an excess of ferroptosis and/or oxytosis occurs.

DETAILED DESCRIPTION

This disclosure will be described with respect to particular embodiments and with reference to certain drawings, but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. The definitions provided herein should not be construed to have a scope less than understood by a person of ordinary skill in the art.

In one embodiment, the disclosure provides a compound depicted in formula (I)

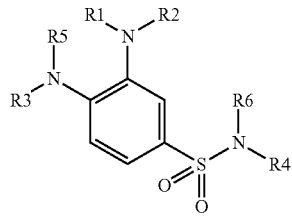

wherein
R1 is selected from the groups consisting of H, C1-C4-alkyl aryl, C1-C4-alkyl pyridine, C1-C4-alkyl pyrimidine, C1-C4-alkyl pyrazine, C1-C4-alkyl pyridazine;
R2 is selected from the groups consisting of H, C1-C4-alkyl aryl, C1-C4-alkyl pyridine, C1-C4-alkyl pyrimidine, C1-C4-alkyl pyrazine, C1-C4-alkyl pyridazine;
R3 is selected from the groups consisting of a C3-C12-cycloalkyl optionally substituted with one or more halogens, optionally replacing one or more carbons by heteroatoms in the cycloalkyl ring structure;
R4 is selected from the groups consisting of a C1-C4-alkyl, wherein the C1-C4 alkyl is optionally terminated with an XR7 group wherein X is a heteroatom and R7 is H or C1-C4 alkyl; in the specific case were XR7 is NR7 the R7 can be only H, or R7 can be H and C1-C4-alkyl, or R7 can be C1-C4-alkyl and C1-C4-alkyl,
R5 is selected from the groups consisting of H or C3-C12-cycloalkyl optionally substituted with one or more halogens, optionally replacing one or more carbons by heteroatoms in the cycloalkyl ring structure;
R6 is selected from the groups consisting of H or a C1-C4-alkyl, wherein in the C1-C4 alkyl the carbon atoms are optionally replaced by one or more heteroatoms;
R4 and R6 can form a C2-C6 cycloalkyl ring structure optionally in the ring structure one or more carbons are replaced by heteroatoms and the ring structure can be substituted by one or more halogens;
Wherein the compounds are not 3-amino-4-(cyclopentylamino)-N,N-sulfonamide (CAS Registry no. 1094762-88-5) and not 3-amino-4-(cyclopropylamino)-N,N-sulfonamide (CAS Registry no. 1094644-45-7)—the latter two compounds are excluded from the scope of the claims of the disclosure.
and pharmaceutically acceptable salts thereof, and individual enantiomers and diasteromers thereof.

In another embodiment, the disclosure provides a compound depicted in formula (I)

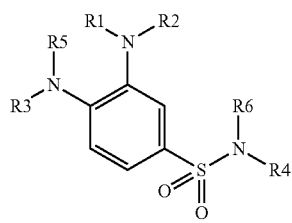

wherein
R1 is selected from the groups consisting of H, methylaryl, ethylaryl, propylaryl, 5 butylaryl, methylpyridine, ethylpyridine, propylpyridine, butylpyridine, methylpyrimidine, ethylpyrimidine, propylpyrimidine, butylpyrimidine, methylpyrazine, ethylpyrazine, propylpyrazine, butylpyrazine, methylpyridazine, ethylpyridazine, propylpyridazine or butylpyridazine;
R2 is selected from the groups consisting of H, methylaryl, ethylaryl, propylaryl, butylaryl, methylpyridine, ethylpyridine, propylpyridine, butylpyridine, methylpyrimidine, ethylpyrimidine, propylpyrimidine, butylpyrimidine, methylpyrazine, ethylpyrazine, propylpyrazine, butylpyrazine, methylpyridazine, ethylpyridazine, propylpyridazine or butylpyridazine;
R3 is selected from the groups consisting of a C3 cycloalkyl, a C4 cycloalkyl, a C5 cycloalkyl, a C6 cycloalkyl, a C7 cycloalkyl, a C8 cycloalkyl, a C9 cycloalkyl, a C10 cycloalkyl, a C11 cycloalkyl, a C12 cycloalkyl, the cycloalkyls are optionally substituted with one or more halogens;
R4 is selected from the groups consisting of a C1-C4-alkyl, wherein the C1-C4 alkyl is optionally terminated with an XR7 group wherein X is a heteroatom and R7 is H or C1-C4 alkyl, specific groups of R4 consist of C1-C4-alkyl, ethanol, propanol, butanol, ethanamine, propanamine and butanamine;
R5 is selected from the groups consisting of H or a C3 cycloalkyl, a C4 cycloalkyl, a C5 cycloalkyl, a C6 cycloalkyl, a C7 cycloalkyl, a C8 cycloalkyl, a C9 cycloalkyl, a C10 cycloalkyl, a C11 cycloalkyl, a C12 cycloalkyl, the cycloalkyls are optionally substituted with one or more halogens;
R6 is selected from the groups consisting of H, C1-C4-alkyl, ethanol, propanol, butanol, ethanamine, propanamine and butanamine
When R4 and R6 form a C2-C6 cycloalkyl, optionally incorporating one or more heteroatoms and the ring structure optionally substituted by one or more halogens and/or a C1-C4 alkyl; the resulting C2-C6 cycloalkyl structures consist of aziridine, azetidine, pyrrolidine, piperidine, azepane, piperazine, N-methylpiperazine, N-ethylpiperazine or morpholine.
and pharmaceutically acceptable salts thereof, and individual enantiomers and diasteromers thereof.

In yet another embodiment, the disclosure provides a compound selected from the list consisting of 3-amino-4-(cyclopropylamino)-N-ethylbenzenesulfonamide, 3-amino-4-(cyclopentylamino)-N-ethylbenzenesulfonamide, 3-amino-4-(cyclohexylamino)-N-ethylbenzenesulfonamide, 3-amino-4-(bicyclo[2.2.1]heptan-2-ylamino)-N-ethylbenzenesulfonamide, 3-amino-4-(cyclooctylamino)-N-ethylbenzenesulfonamide, 4-(adamantan-2-ylamino)-3-amino-N-ethylbenzenesulfonamide, 3-amino-4-(cyclohexylamino)-N-methylbenzenesulfonamide, 4-(adamantan-2-ylamino)-3-amino-N-methylbenzenesulfonamide, 3-amino-N-(tert-butyl)-4-(cyclohexylamino)benzenesulfonamide, 4-(adamantan-2-ylamino)-3-amino-N-(tert-butyl)benzenesulfonamide, 3-amino-N-(2-(tert-butoxy)ethyl)-4-(cyclohexylamino)benzenesulfonamide, N1-cyclohexyl-4-((4-methylpiperazin-1-yl)sulfonyl)benzene-1,2-diamine, N1-cyclohexyl-4-(morpholinosulfonyl)benzene-1,2-diamine, 3-(benzylamino)-4-(cyclopropylamino)-N-ethylbenzenesulfonamide, 4-(cyclopropylamino)-N-ethyl-3-((pyridin-4-ylmethyl)amino)benzenesulfonamide, 3-(benzylamino)-4-(cyclopentylamino)-N-ethylbenzenesulfonamide, 4-(cyclopentylamino)-N-ethyl-3-((pyridin-4-ylmethyl)amino)benzenesulfonamide, 3-(benzylamino)-4-(cyclohexylamino)-N-ethylbenzenesulfonamide, 4-(cyclohexylamino)-N-ethyl-3-((pyridin-4-ylmethyl) amino)benzenesulfonamide, 4-(cyclohexylamino)-N-ethyl-3-((pyrimidin-5-ylmethyl)amino)benzenesulfonamide, 3-(benzylamino)-4-(bicyclo[2.2.1]heptan-2-ylamino)-N-ethylbenzenesulfonamide, 4-(bicyclo[2.2.1]heptan-2-ylamino)-N-ethyl-3-((pyridin-4-ylmethyl)amino)benzenesulfonamide, 3-(benzylamino)-4-(cyclooctylamino)-N-ethylbenzenesulfonamide, 4-(cyclooctylamino)-N-ethyl-3-((pyridin-4-ylmethyl)amino)benzenesulfonamide, 4-(adamantan-2-ylamino)-3-(benzylamino)-N-ethylbenzenesulfonamide, 4-(adamantan-2-ylamino)-N-ethyl-3-((pyridin-4-ylmethyl)amino)benzenesulfonamide, 4-(adamantan-2-ylamino)-N-ethyl-3-((pyrimidin-5-ylmethyl)amino) benzenesulfonamide, 3-(benzylamino)-4-(cyclohexylamino)-N-methylbenzenesulfonamide, 4-(cyclohexylamino)-N-methyl-3-((pyridin-4-ylmethyl) amino)benzenesulfonamide, 4-(adamantan-2-ylamino)-3-(benzylamino)-N-methylbenzenesulfonamide, 4-(adamantan-2-ylamino)-N-methyl-3-((pyridin-4-ylmethyl)amino) benzenesulfonamide, 3-(benzylamino)-N-(tert-butyl)-4-(cyclohexylamino)benzenesulfonamide, N-(tert-butyl)-4-(cyclohexylamino)-3-((pyridin-4-ylmethyl)amino) benzenesulfonamide, 4-(adamantan-2-ylamino)-3-(benzylamino)-N-(tert-butyl)benzenesulfonamide, 4-(adamantan-2-ylamino)-N-(tert-butyl)-3-((pyridin-4-ylmethyl)amino)benzenesulfonamide, 3-(benzylamino)-N-(2-(tert-butoxy)ethyl)-4-(cyclohexylamino)benzenesulfonamide, N2-benzyl-N1-cyclohexyl-4-((4-methylpiperazin-1-yl)sulfonyl)benzene-1,2-diamine and N2-benzyl-N1-cyclohexyl-4-(morpholinosulfonyl)benzene-1,2-diamine, 3-(benzylamino)-4-(cyclohexylamino)-N-(2-hydroxyethyl) benzenesulfonamide.

Any of the compounds according to the disclosure can exist as one or more stereoisomers depending on the number of stereogenic centers (as defined by the IUPAC rules) in the compound. The disclosure thus relates equally to all the stereoisomers, and to the mixtures of all the possible stereoisomers, in all proportions. Typically one of the stereoisomers has enhanced biological activity compared to the other possibilities. The stereoisomers can be separated according to the methods that are known per se by the man ordinary skilled in the art. Similarly, where there are disubstituted alkenes, these may be present in E or Z form or as mixtures of both in any proportion. Furthermore it should be appreciated that all tautomeric forms (single tautomer or mixtures thereof), racemic mixtures and single isomers of compounds of formula (I) are included within the scope of this disclosure.

The disclosure also includes salts that the compounds of formula (I) may form with amines (for example, ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium. The corresponding trimethylsulfonium salt may also be used.

The term "C1-C4-alkyl" refers to a linear or branched-chain saturated, mono-unsaturated and poly-unsaturated hydrocarbyl substituent (i.e., a substituent obtained from a hydrocarbon by removal of a hydrogen) containing one (1), two (2), three (3) or four (4) carbon atoms. Mono- and poly-unsaturated substituents, also called alkenyl, have 2 to 4 carbon atoms. The alkenyl group may exist as the pure E (entgegen) form, the pure Z (zusammen) form, or any mixture thereof. Poly-unsaturated includes multiple double bonds and one or more triple bonds. Such triple bond containing alkyl groups, a so called alkynyl group, has 2 to 4 carbon atoms. Examples of such saturated substituents include methyl, ethyl, propyl (including n-propyl and iso-propyl) and butyl (including n-butyl, isobutyl, sec-butyl and tert-butyl). Examples of unsaturated alkyl include ethenyl, 1-propenyl, 2-propenyl (allyl), iso-propenyl, 2-methyl-1-propenyl, 1-butenyl, 2-butenyl, and the like. Examples of alkynyl include ethynyl, propynyl, butynyl, 3,3-dimethyl-butynyl and the like.

The term "C3-C12 cycloalkyl", as used herein, refers to the radical of saturated aliphatic groups having a ring structure. Certain cycloalkyls have from 3-12 carbon groups in their ring structure, including 3, 4, 5, 6, 7, 8, 9, 10, 11 or 12 carbons in the ring structure. A preferred cycloalkyl structure is the adamantan (C10) structure. Cycloalkyls can be further substituted with one or more C1-C4 alkyls, one or more C1-C4 alkenyls, one or more C1-C4 alkoxys, one or more C1-C4 alkylthios, one or more C1-C4 aminoalkyls, one or more CF3, one or more —CN and/or one or more halogens. Carbon atoms present in the C3-C12 cycloalkyls can be optionally replaced by one or more heteroatoms in the ring structure, particularly preferred heteroatoms are N, O and S.

The term "aryl" as used herein includes substituted or unsubstituted single-ring aromatic groups in which each atom of the ring is carbon, or nitrogen (if ring carbons are substituted). Preferably the ring is a 3- to 8-membered ring, more preferably a 6-membered ring. The term "aryl" also includes polycyclic ring system having two or more cyclic rings in which two or more carbons are common to two adjoining rings wherein at least one of the rings is aromatic. Aryl groups include benzene, naphthalene, phenol, aniline and the like.

The term "cyano" (also referred to as "nitrile") means —CN, which also may be depicted as —C≡N.

The term "alkoxy" refers to an alkyl linked to an oxygen, which may also be represented as: —O—R, wherein the R represents the alkyl group. Examples of alkoxy include methoxy, ethoxy, propoxy and butoxy.

The term "halogen" includes chloro, fluoro, bromo and iodo. Preferred halogens are chloro and fluoro.

The term "heteroatom" refers to any atom that is not carbon in a structure, oxygen (O), nitrogen (N), sulfur (S) or phosphor (P) are preferred heteroatoms, most preferred heteroatoms are N, S or O. In this disclosure, a heteroatom is used in the context of the replacement of a carbon (C) atom for a heteroatom in the backbone of a molecular structure such as, for example, a carbon that is replaced in N or O in a C1-C4 alkyl or in a C3-C12 cycloalkyl.

The term "substituent" refers to an atom, for example, a halogen, or group of atoms substituted in place of a hydrogen atom on the chain of a hydrocarbon.

If substituents are described as being "independently selected" from a group, each substituent is selected independent of the other. Each substituent therefore may be identical to or different from the other substituent(s).

When an asymmetric center is present in a compound of formula (I) hereinafter referred to as a "compound of the disclosure," the compound may exist in the form of optical isomers (enantiomers). In one embodiment, this disclosure comprises enantiomers and mixtures, including racemic mixtures of the compounds of formula I. In another embodiment, for compounds of formula I that contain more than one asymmetric center, the disclosure comprises diastereomeric forms (individual diastereomers and mixtures thereof) of compounds. When a compound of formula I contains an alkenyl group or moiety, geometric isomers may arise.

This disclosure comprises the tautomeric forms of compounds of formula I. Where structural isomers are interconvertible via a low energy barrier, tautomeric isomerism ("tautomerism") can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

Suitable pharmaceutically acceptable acid addition salts of the compounds of the disclosure when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Furthermore, where the compounds of the disclosure carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts. In one embodiment, hemisalts of acids and bases may also be formed, for example, hemisulphate and hemicalcium salts.

This disclosure also includes isotopically labelled compounds, which are identical to those recited in formula I, but for the fact that one or more atoms are replaced by an atom having an atomic mass or mass number different from the atomic mass or mass number usually found in nature. Examples of isotopes that may be incorporated into compounds of the disclosure include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the disclosure and pharmaceutically acceptable salts of the compounds or which contain the aforementioned isotopes and/or other isotopes of other atoms are within the scope of this disclosure. Certain isotopically labeled compounds of the disclosure, for example, those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example, increased in vivo half-life or reduced dosage requirements and, hence, may be preferred in some circumstances, isotopically labelled compounds of formula I of this disclosure may generally be prepared by carrying out the procedures disclosed in the Schemes and/or in the Examples and Preparations below, by substituting a readily available isotopically labelled reagent for a non-isotopically labelled reagent.

This disclosure also relates to pharmaceutical compositions containing one or more compounds of the disclosure. These compositions can be utilized to achieve the desired pharmacological effect by administration to a patient in need thereof. A patient, for the purpose of this disclosure, is a mammal, including a human, in need of treatment for the particular condition or disease. Therefore, the disclosure includes pharmaceutical compositions that are comprised of a pharmaceutically acceptable carrier and a pharmaceutically effective amount of a compound, or salt thereof, of this disclosure. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the disclosure can be administered with pharmaceutically-acceptable carriers well known in the art using any effective conventional dosage unit forms, including immediate, slow and timed release preparations, orally, parenterally, topically, nasally, ophthalmically, optically, intrathecally, intracerebroventricularly, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of the disclosure may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example, talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this disclosure may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of the partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin. Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents. The compounds of the disclosure may also be administered parenterally, that is, subcutaneously, intravenously, intraocularly, intrasynovially, intramuscularly, or intraperitoneally, as injectable dosages of the compound in preferably a physiologically acceptable diluent with a pharmaceutical carrier, which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1, 1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this disclosure are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this disclosure will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the disclosure may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the disclosure employs transdermal delivery devices ("patches"). Such transdermal patches may be used to provide continuous or discontinuous infusion of the compounds of the disclosure in controlled amounts. The construction and use of transdermal patches for the delivery of pharmaceutical agents is well known in the art (see, for example, U.S. Pat. No. 5,023,252). Such patches may be constructed for continuous, pulsatile, or on demand delivery of pharmaceutical agents. Controlled release formulations for parenteral administration include liposomal, polymeric microsphere and polymeric gel formulations that are known in the art. It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472.

The compositions of the disclosure can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: M. F. Powell et al., "Compendium of Excipients for Parenteral Formulations," *PDA Journal of Pharmaceutical Science & Technology* 1998, 52(5), 238-311; R. G. Strickley, "Parenteral Formulations of Small Molecule Therapeutics Marketed in the United States (1999)-Part-1" *PDA Journal of Pharmaceutical Science & Technology* 1999, 53(6), 324-349; and S. Nema et al., "Excipients and Their Use in Injectable Products" *PDA Journal of Pharmaceutical Science & Technology* 1997, 51 (4), 166-171.

Commonly used pharmaceutical ingredients that can be used as appropriate to formulate the composition for its intended route of administration include:

acidifying agents (examples include, but are not limited to, acetic acid, citric acid, fumaric acid, hydrochloric acid, nitric acid); alkalinizing agents (examples include, but are not limited to, ammonia solution, ammonium carbonate, diethanolamine, monoethanolamine, potassium hydroxide, sodium borate, sodium carbonate, sodium hydroxide, triethanolamine, trolamine); adsorbents (examples include, but are not limited to, powdered cellulose and activated charcoal); aerosol propellants (examples include, but are not limited to, carbon dioxide, $CCl_2F_2$, $F_2ClC$—$CClF_2$ and $CClF_3$) air displacement agents (examples include, but are not limited to, nitrogen and argon); antifungal preservatives (examples include, but are not limited to, benzoic acid, butylparaben, ethylparaben, methylparaben, propylparaben, sodium benzoate); antimicrobial preservatives (examples include, but are not limited to, benzalkonium chloride, benzethonium chloride, benzyl alcohol, cetylpyridinium chloride, chlorobutanol, phenol, phenylethyl alcohol, phenylmercuric nitrate and thimerosal); antioxidants (examples include, but are not limited to, ascorbic acid, ascorbyl palmitate, butylated hydroxyanisole, butylated hydroxytoluene, hypophosphorus acid, monothioglycerol, propyl gallate, sodium ascorbate, sodium bisulfate, sodium formaldehyde sulfoxylate, sodium metabisulfite); binding materials (examples include, but are not limited to, block polymers, natural and synthetic rubber, polyacrylates, polyurethanes, silicones, polysiloxanes and styrene-butadiene copolymers); buffering agents (examples include, but are not limited to, potassium metaphosphate, dipotassium phosphate, sodium acetate, sodium citrate anhydrous and sodium citrate dihydrate) carrying agents (examples include, but are not limited to, acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection) chelating agents (examples include, but are not limited to, edetate disodium and edetic acid) colorants (examples include, but are not limited to, FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include, but are not limited to, bentonite);

emulsifying agents (examples include, but are not limited to, acacia, cetomacrogol, cetyl alcohol, glyceryl monostearate, lecithin, sorbitan monooleate, polyoxyethylene 50 monostearate);

encapsulating agents (examples include, but are not limited to, gelatin and cellulose acetate phthalate);

flavorants (examples include, but are not limited to, anise oil, cinnamon oil, cocoa, menthol, orange oil, peppermint oil and vanillin);

humectants (examples include, but are not limited to, glycerol, propylene glycol and sorbitol);

levigating agents (examples include, but are not limited to, mineral oil and glycerin);

oils (examples include, but are not limited to, arachis oil, mineral oil, olive oil, peanut oil, sesame oil and vegetable oil);

ointment bases (examples include, but are not limited to, lanolin, hydrophilic ointment, polyethylene glycol ointment, petrolatum, hydrophilic petrolatum, white ointment, yellow ointment, and rose water ointment);

penetration enhancers (transdermal delivery) (examples include, but are not limited to, monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include, but are not limited to, diethyl phthalate and glycerol);

solvents (examples include, but are not limited to, ethanol, corn oil, cottonseed oil, glycerol, isopropanol, mineral oil, oleic acid, peanut oil, purified water, water for injection, sterile water for injection and sterile water for irrigation);

stiffening agents (examples include, but are not limited to, cetyl alcohol, cetyl esters wax, microcrystalline wax, paraffin, stearyl alcohol, white wax and yellow wax);

suppository bases (examples include, but are not limited to, cocoa butter and polyethylene glycols (mixtures);

surfactants (examples include, but are not limited to, benzalkonium chloride, nonoxynol 10, oxtoxynol 9, polysorbate 80, sodium lauryl sulfate and sorbitan mono-palmitate);

suspending agents (examples include, but are not limited to, agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include, but are not limited to, aspartame, dextrose, glycerol, mannitol, propylene glycol, saccharin sodium, sorbitol and sucrose);

tablet anti-adherents (examples include, but are not limited to, magnesium stearate and talc);

tablet binders (examples include, but are not limited to, acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include, but are not limited to, dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include, but are not limited to, liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include, but are not limited to, dibasic calcium phosphate);

tablet disintegrants (examples include, but are not limited to, alginic acid, carboxymethylcellulose calcium, microcrystalline cellulose, polacrillin potassium, cross-linked polyvinylpyrrolidone, sodium alginate, sodium starch glycolate and starch);

tablet glidants (examples include, but are not limited to, colloidal silica, corn starch and talc);

tablet lubricants (examples include, but are not limited to, calcium stearate, magnesium stearate, mineral oil, stearic acid and zinc stearate);

tablet/capsule opaquants (examples include, but are not limited to, titanium dioxide);

tablet polishing agents (examples include, but are not limited to, carnuba wax and white wax);

thickening agents (examples include, but are not limited to, beeswax, cetyl alcohol and paraffin);

tonicity agents (examples include, but are not limited to, dextrose and sodium chloride);

viscosity increasing agents (examples include, but are not limited to, alginic acid, bentonite, carbomers, carboxymethylcellulose sodium, methylcellulose, polyvinyl pyrrolidone, sodium alginate and tragacanth); and wetting agents (examples include, but are not limited to, heptadecaethylene oxycetanol, lecithins, sorbitol monooleate, polyoxyethylene sorbitol monooleate, and polyoxyethylene stearate).

Pharmaceutical compositions according to the disclosure can be illustrated as follows:

Sterile IV Solution: A between 0.01-5 mg/mL solution of the desired compound of this disclosure can be made using sterile, injectable water, and the pH is adjusted if necessary. The solution is diluted for administration to 0.02-2 mg/mL with sterile 5% dextrose and is administered as an IV infusion over about 60 minutes.

Lyophilized powder for IV administration: A sterile preparation can be prepared with (i) 1-1000 mg of the desired compound of this disclosure as a lyophilized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

0.01-5 mg/mL of the desired, water-insoluble compound of this disclosure
5 mg/mL sodium carboxymethylcellulose
4 mg/mL TWEEN® 80
9 mg/mL sodium chloride
9 mg/mL benzyl alcohol Hard Shell Capsules: A large number of unit capsules are prepared by filling standard two-piece hard galantine capsules each with 1-100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 1-100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 1-100 mg of active ingredient, 0.2 mg of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Therapeutic Uses of the Compounds of the Disclosure

In another particular embodiment, the disclosure provides the compounds of the disclosure or a pharmaceutical composition comprising one or more compounds of the disclosure for the inhibition of ferroptosis.

In another particular embodiment, the disclosure provides the compounds of the disclosure or a pharmaceutical composition comprising one or more compounds of the disclosure for the inhibition of oxytosis.

In another particular embodiment, the disclosure provides the compounds of the disclosure or a pharmaceutical composition comprising one or more compounds of the disclosure for the inhibition of oxytosis and ferroptosis.

In another particular embodiment, the disclosure provides the compounds of the disclosure or a pharmaceutical composition comprising one or more compounds of the disclosure for the treatment of a mammal suffering from excessive ferroptosis in one or more organs.

In another particular embodiment, the disclosure provides the compounds of the disclosure or a pharmaceutical composition comprising one or more compounds of the disclosure for the treatment of a mammal suffering from excessive oxytosis in one or more organs.

In another particular embodiment, the disclosure provides the compounds of the disclosure or a pharmaceutical composition comprising one or more compounds of the disclosure for the treatment of a mammal suffering from excessive ferroptosis and oxytosis in one or more organs.

In another particular embodiment, the disclosure provides the compounds of the disclosure or a pharmaceutical composition comprising one or more compounds of the disclosure for the treatment of diseases caused by excitatory amino acids. A well-known example of an excitatory amino acid is glutamine and the condition is designated as glutamine excitotoxicity.

In another particular embodiment, the disclosure provides the compounds of the disclosure or a pharmaceutical composition comprising one or more compounds of the disclosure for the treatment of diseases caused by increased levels of intracellular reactive oxygen species (ROS).

In another particular embodiment, the disclosure provides the compounds of the disclosure or a pharmaceutical composition comprising one or more compounds of the disclosure for the treatment of stroke, myocardial infarction, diabetes, sepsis, neurodegenerative diseases including Alzheimer's Disease, Parkinson's Disease, Amyotrophic lateral sclerosis, Huntington's Disease, Dementia with Lewy bodies, Friedreich's ataxia and multiple sclerosis. In a particular embodiment, the disclosure provides the compounds of the disclosure or a pharmaceutical composition comprising one or more compounds of the disclosure for use in the prevention of transplant rejection. Thus the compounds can be used during the kidney, liver or heart transplantation to prevent organ damage due to ischemia-reperfusion injury.

In the present disclosure, the potency of a compound inhibiting (or reducing) ferroptosis and/or oxytosis are determined in in vitro or in vivo assays. Typically in vitro assays are used to measure the potency of a candidate compound. Examples of suitable in vitro assays are cellular assays. One non-limiting example of an assay involves the use of the IMR-32 neuroblastoma cell line. The latter is stimulated to enter into ferroptosis upon stimulation with 10 µM erastin, a documented ferroptosis inducer (see, for example, Dixon et al. (2012) *Cell* 149, 1060-1072, and ferroptosis inhibitors are evaluated for the prevention of erastin-induced ferroptosis. Yet another assay is based the glutamate-induced cell death in the hippocampal cell line HT22 and ferroptosis/oxytosis inhibitors are evaluated for the prevention of cell death (see N. Henke et al. (2013) *Cell Death and Disease* 4, e470). Still another assay is based on the sorafinib-induced cell death (described to be iron dependent cell death) in hepatocellular carcinoma cells and ferroptosis inhibitors are evaluated for the prevention of cell death (see C. Louandre et al. (2013) *Int. J. Cancer* 133, 1732). The calculated potency of a compound inhibiting ferroptosis and/or oxytosis is typically depicted as an IC50 value. Examples of suitable in vivo assays are typically pre-clinical disease models of, for example, mice for the diseases benefiting the application of ferroptosis and/or oxytosis inhibitors, as described herein. One non-limiting example of an in vivo assay is based on inducing liver damage in mice by administering the herbicide diquat dibromide monohydrate and ferroptosis inhibitors are evaluated based on reduced levels of liver transaminases in serum (see Q. Ran et al. (2004) *J. Biol. Chem.* 279, 53, 55137).

Combination Therapies:

The compounds of the disclosure can be administered as the sole pharmaceutical agent or in combination with one or more other pharmaceutical agents where the combination causes no unacceptable adverse effects. This disclosure relates also to such combinations. For example, the compounds of the disclosure can be combined with known therapeutic agents for the treatment of diseases mentioned herein, as well as with admixtures and combinations thereof. Particularly preferred combinations are necroptosis inhibitors (e.g., necrostatin-1) and ferroptosis inhibitors. Examples of these combinations are described in Linkerman et al. 2014.

The term "treating" or "treatment" as stated throughout this document is used conventionally, e.g., the management or care of a subject for the purpose of combating, alleviating, reducing, relieving, improving the condition of a disease cited herein.

Dose and Administration:

Based upon standard laboratory techniques known to evaluate compounds useful for the treatment of diseases cited herein, by standard toxicity tests and by standard pharmacological assays for the determination of treatment of the conditions identified above in mammals, and by comparison of these results with the results of known medicaments that are used to treat these conditions, the effective dosage of the compounds of this disclosure can readily be determined for treatment of the indications cited herein. The amount of the active ingredient to be administered in the treatment can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 50 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight. The average daily oral dosage regimen will preferably be from 0.01 to 100 mg/kg of total body weight. The average daily intrathecal dosage regimen will preferably be from 0.01 to 100 mg/kg of total body weight.

It is evident for the skilled artisan that the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of this disclosure or a pharmaceutically acceptable salt or ester or composition thereof can be ascertained by those skilled in the art using conventional treatment tests.

Experimental Procedures for Chemical Synthesis

Unless otherwise stated, laboratory reagent grade solvents were used. Reagents were obtained from Sigma-Aldrich, Acros Organics or Fluorochem and were used without further purification. Characterization of all compounds was done with $^1$H and $^{13}$C NMR and mass spectrometry. $^1$H and $^{13}$C NMR spectra were recorded on a 400 MHz Bruker Avance III Nanobay spectrometer with Ultrashield and analyzed by use of MestReNova analytical chemistry software. Chemical shifts are in ppm, and coupling constants are in hertz (Hz). ES mass spectra were obtained from an Esquire 3000 plus ion trap mass spectrometer from Bruker Daltonics. Purities were determined with two diverse HPLC systems based either on mass determination or on UV detection. A Waters acquity UPLC system coupled to a Waters TQD ESI mass spectrometer or a Waters SQD ESI mass spectrometer was used both in combination with a Waters TUV detector. Water (A) and CH$_3$CN (B) were used as eluents. LC-MS spectra were recorded on an Agilent 1100 series HPLC system using a Alltech Prevail C18 column (2.1 mm×50 mm, 3 µm) coupled with an Esquire 3000 plus as MS detector, and a "method A" 5-100% B, 20 min gradient was used with a flow rate of 0.2 mL/min. Formic acid, 0.1%, was added to solvents A and B. Waters Acquity UPLC BEH C18 1.7 µm, 2.1 mm×50 mm column was used. Solvent A consisted of water with 0.1% formic acid. Solvent B consisted of acetonitrile with 0.1% formic acid. Method I involved the following: 0.15 min 95% A, 5% B, then in 1.85 min from 95% A, 5% B to 95% B, 5% A, then 0.25 min (0.350 mL/min), 95% B, 5% A. The wavelength for UV detection was 254 nm. Method II involved the following: flow 0.4 mL/min, 0.25 min 95% A, 5% B, then in 4.75 min to 95% B, 5% A, then 0.25 min 95% B, 5% A, followed by 0.75 min 95% A, 5% B. The wavelength for UV detection was 214 nm. Where necessary, flash purification was performed on a Biotage ISOLERA One flash system equipped with an internal variable dual wavelength diode array detector (200-400 nm). For normal phase purifications SNAP cartridges (10-340 g, flow rate of 10-100 mL/min) were used, and reversed phase purifications were done making use of KP-C18 containing cartridges. Dry sample loading was done by self-packing samplet cartridges using silica and Celite 545, respectively, for normal and reversed phase purifications. Gradients used varied for each purification. Mouse and rat plasma came from Innovative Research. The turbidity in the kinetic solubility experiments was measured using the UV/vis spectrophotometer Synergy MX, Biotek with Gen5.

Examples

1. Chemical Synthesis of Representative Compounds of the Invention

Chemistry

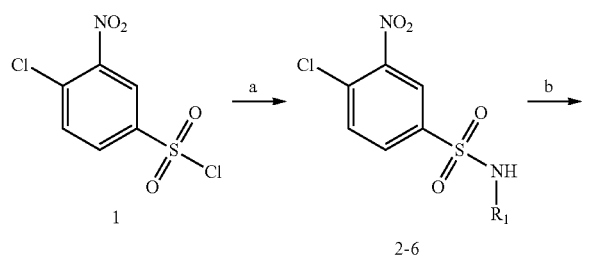

Scheme 1: Reagents and conditions: (a) amine analogue, triethylamine, THF, 1 hour, −40° C. to rt; (b) cyclohexylamine or 2-adamantylamine.HCl, K$_2$CO$_3$, DMSO, 17 hours, 60° C.;[1] (c) Pd(OH)$_2$, H$_2$ gas, MeOH, 17 hours, rt; Error! Bookmark not defined. (d) benzylbromide or 4-(bromomethyl)pyridinehydrobromide, K$_2$CO$_3$, DMF, 1-4 hours, 60° C.

Scheme 1 shows the synthesis of sulfonamide analogues of ferrostatin-1. The derivates were synthesized from 4-chloro-3-nitrobenzenesulfonyl chloride 1 by reaction of the appropriate amine analog with sulfonylchloride, which delivered 2-6. Nucleophilic aromatic substitution of 2-6 with different cycloalkylamines in basic conditions resulted in 7-19. Palladium-catalyzed reduction of the 3-nitro group resulted in 20-31 and coupling of the resulting 3-amines with benzylamine or pyridin-4-ylmethanamine resulted in target compounds 32-57.

Experimental Section

General Procedure A

A solution of 4-chloro-3-nitrobenzene-1-sulfonyl chloride (1 equiv.) in THF was cooled down to −40° C. before being treated with the appropriate amine analog (1 equiv.) followed by triethylamine (2 equiv.). The reaction mixture was stirred and allowed to reach room temperature over 1 hour. The reaction mixture was diluted with EtOAc, washed twice with brine and dried. The residue was purified by flash-column chromatography on silica gel (EtOAc in heptane) to provide the desired sulfonamide analogues 2-6.

General Procedure B

To the appropriate 4-chloro-3-nitrobenzenesulfonamide intermediate 2-6 (1 equiv.) in dry DMSO was added $K_2CO_3$ (2-4 equiv.) and the appropriate cycloalkylamine analog (1.2 equiv.). The mixture was stirred for 17 hours at 60° C. The solution was poured in water, extracted with 3× ethyl acetate and dried with $MgSO_4$. The solvent was removed under reduced pressure. The residue was purified by flash-column chromatography on silica gel to respectively provide the desired 4-(cycloalkylamino)-3-nitrobenzenesulfonamide analogues 7-19.

General Procedure C

The appropriate 4-(cycloalkylamino)-3-nitrobenzenesulfonamide intermediate 7-19 (1 equiv.) was dissolved in methanol, flushed with argon and hydrogenated ($H_2$ gas) over 10% $Pd(OH)_2$ (1.5 equiv.) for 17 hours at room temperature. The solution was filtered through a pad of celite and volatiles were removed under reduced pressure. If necessary, the residue was purified by flash-column chromatography on silica gel to provide the desired 4-(cycloalkylamino)-3-aminobenzenesulfonamide analog 20-31.

General Procedure D

To the 4-(cycloalkylamino)-3-aminobenzenesulfonamide intermediate 20-31 (1 equiv.) in DMF was added the appropriate benzyl or pyridinyl derivate (1-2 equiv.) and $K_2CO_3$ (2-4 equiv.). The mixture was stirred at 60° C. for 1-4 hours then poured in water. The organic layer was extracted with 3× EtOAc and the solvent was removed under reduced pressure. The residue was purified by flash-column chromatography on silica gel to respectively provide sulfonamide compounds 32-58.

4-chloro-N-methyl-3-nitrobenzenesulfonamide (2)

Following general procedure A and methylamine hydrochloride as the corresponding amine, the reaction was purified by flash-column chromatography on silica gel (50% ethyl acetate in heptane) to afford the desired afford 4-chloro-N-ethyl-3-nitrobenzenesulfonamide (2.98 g, 11.99 mmol). (Yield: 60.9%)

$^1$H NMR (400 MHz, DMSO-$d_6$) δ 2.50 (s, 4H), 7.86 (s, 1H), 8.03-8.05 (m, 2H), 8.42 (dd, J=0.89, 1.64 Hz, 1H). $^{13}$C NMR (101 MHz, DMSO-$d_6$) δ 29.10, 124.55, 129.82, 131.95, 133.60, 140.05, 147.94.

MS (ESI) m/z 499 [M+]

4-chloro-N-ethyl-3-nitrobenzenesulfonamide (3)

Following general procedure A and ethylamine hydrochloride as the corresponding amine, the reaction was purified by flash-column chromatography on silica gel (10% methanol in dichloromethane) to afford the desired afford 4-chloro-N-ethyl-3-nitrobenzenesulfonamide (3.5 g, 13.22 mmol). (Yield: 72.0%)

$^1$H NMR (400 MHz, CDCl$_3$) δ 1.19 (t, J=7.24 Hz, 3H), 3.12 (qd, J=5.71, 7.23 Hz, 2H), 4.71 (s, 1H), 7.75 (dd, J=0.37, 8.39 Hz, 1H), 8.02 (dd, J=2.16, 8.43 Hz, 1H), 8.38 (dd, J=0.55, 2.02 Hz, 1H). $^{13}$C NMR (101 MHz, CDCl$_3$) δ 15.20, 38.51, 124.40, 131.07, 131.55, 133.01, 140.53, 147.91.

MS (ESI) m/z 265 [M+H]

4-chloro-N-(tert-butyl)-3-nitrobenzenesulfonamide (4)

Following general procedure A and tert.-butylamine as the corresponding amine, the reaction was purified by flash-column chromatography on silica gel (50% ethyl acetate in heptane) to afford the desired afford 4-chloro-N-(tert-butyl)-3-nitrobenzenesulfonamide (2.1 g, 7.17 mmol). (Yield: 92.0%)

$^1$H NMR (400 MHz, DMSO-$d_6$) δ 1.14 (s, 9H), 7.93 (s, 1H), 8.00 (d, J=8.47 Hz, 1H), 8.10 (dd, J=2.19, 8.45 Hz, 1H), 8.48 (d, J=2.15 Hz, 1H). $^{13}$C NMR (101 MHz, DMSO-$d_6$) δ 30.18, 54.45, 124.12, 129.19, 131.52, 133.47, 144.96, 147.78.

MS (ESI) m/z 291 [M+]

N-(2-(tert-butoxy)ethyl)-4-chloro-3-nitrobenzenesulfonamide (5)

Following general procedure A and 2-(tert-butoxy)ethanamine (7.81 mmol) as the corresponding amine, the reaction was purified by flash-column chromatography on silica gel (10% methanol in dichloromethane) to afford the desired afford N-(2-(tert-butoxy)ethyl)-4-chloro-3-nitrobenzenesulfonamide (2.0 g, 5.94 mmol). (Yield: 76.0%)

$^1$H NMR (400 MHz, DMSO-$d_6$) δ 1.03 (s, 9H), 2.97 (t, J=5.71 Hz, 2H), 3.28 (t, J=5.74 Hz, 2H), 8.02 (d, J=8.41 Hz, 1H), 8.07 (dd, J=2.10, 8.46 Hz, 2H), 8.44 (d, J=2.07 Hz, 1H). $^{13}$C NMR (101 MHz, DMSO-$d_6$) δ 27.56, 43.90, 60.55, 72.95, 124.34, 129.49, 131.77, 133.42, 141.82, 147.89.

1-((4-chloro-3-nitrophenyl)sulfonyl)-4-methylpiperazine (6)

Following general procedure A and 1-methylpiperazine as the corresponding amine, the reaction was purified by flash-column chromatography on silica gel (10% methanol in dichloromethane) to afford the desired afford 1-((4-chloro-3-nitrophenyl)sulfonyl)-4-methylpiperazine (2.0 g, 7.81 mmol). (Yield: 72.1%)

$^1$H NMR (400 MHz, DMSO-$d_6$) δ 2.16 (s, 3H), 2.37 (t, J=4.97 Hz, 4H), 3.00 (t, J=5.16 Hz, 4H), 8.00-8.08 (m, 2H), 8.39 (dd, J=0.47, 2.12 Hz, 1H). $^{13}$C NMR (101 MHz, Acetone-$d_6$) δ 45.04, 46.01, 53.85, 124.78, 130.61, 132.10, 133.15, 136.54, 148.20.

4-(cyclopropylamino)-N-ethyl-3-nitrobenzenesulfonamide (7)

Following general procedure B, using 4-chloro-N-ethyl-3-nitrobenzenesulfonamide (0.500 g, 1.889 mmol) and cyclopropanamine (0.159 ml, 2.267 mmol). The reaction was purified by flash-column chromatography on silica gel (35% ethyl acetate in heptane) to afford the desired 4-(cyclopropylamino)-N-ethyl-3-nitrobenzenesulfonamide (0.437 g, 1.532 mmol). (Yield: 81.0%)

$^1$H NMR (400 MHz, DMSO-d$_6$) δ 0.67-0.72 (m, 2H), 0.89-0.94 (m, 2H), 0.99 (t, J=7.21 Hz, 3H), 2.69-2.74 (m, 1H), 2.79 (td, J=5.67, 7.23 Hz, 2H), 7.53-7.58 (m, 2H), 7.89 (ddd, J=0.68, 2.29, 9.09 Hz, 1H), 8.37-8.39 (m, 1H), 8.42 (d, J=2.22 Hz, 1H). $^{13}$C NMR (101 MHz, DMSO-d$_6$) δ 8.01, 15.14, 25.43, 37.98, 117.22, 125.95, 127.50, 130.70, 133.62, 148.14.

MS (ESI) m/z 286 [M+H]

4-(cyclopentylamino)-N-ethyl-3-nitrobenzenesulfonamide (8)

Following general procedure B, using 4-chloro-N-ethyl-3-nitrobenzenesulfonamide (1 g, 3.78 mmol) and cyclopentanamine (0.449 ml, 4.53 mmol). The reaction was purified by flash-column chromatography on silica gel (70% ethyl acetate in heptane) to afford the desired 4-(cyclopentylamino)-N-ethyl-3-nitrobenzenesulfonamide (1.003 g, 3.20 mmol). (Yield: 85.0%)

$^1$H NMR (400 MHz, DMSO-d$_6$) δ 0.99 (t, J=7.21 Hz, 3H), 1.54-1.66 (m, 4H), 1.70-1.78 (m, 2H), 2.05-2.15 (m, 2H), 2.77 (q, J=7.22 Hz, 2H), 4.12 (p, J=6.04, 6.52 Hz, 1H), 7.29 (d, J=9.19 Hz, 1H), 7.54 (s, 1H), 7.81 (ddd, J=0.67, 2.33, 9.19 Hz, 1H), 8.27 (d, J=6.73 Hz, 1H), 8.43 (d, J=2.24 Hz, 1H). $^{13}$C NMR (101 MHz, DMSO-d$_6$) δ 15.13, 24.05, 33.07, 37.97, 54.42, 116.77, 126.34, 126.68, 130.27, 133.75, 146.77.

MS (ESI) m/z 314 [M+H]

4-(cyclohexylamino)-N-ethyl-3-nitrobenzenesulfonamide (9)

Following general procedure B, using 4-chloro-N-ethyl-3-nitrobenzenesulfonamide (1 g, 3.78 mmol) and cyclohexanamine (0.519 ml, 4.53 mmol). The reaction was purified by flash-column chromatography on silica gel (5% methanol in dichloromethane) to afford the desired 4-(cyclohexylamino)-N-ethyl-3-nitrobenzenesulfonamide (0.95 g, 2.90 mmol). (Yield: 77.0%)

$^1$H NMR (400 MHz, CDCl$_3$) δ 1.13 (t, J=7.24 Hz, 3H), 1.29-1.52 (m, 5H), 1.63-1.72 (m, 1H), 1.77-1.88 (m, 2H), 2.00-2.13 (m, 2H), 3.01 (qd, J=5.92, 7.21 Hz, 2H), 3.52-3.65 (m, 1H), 5.04 (t, J=5.98 Hz, 1H), 6.99 (d, J=9.17 Hz, 1H), 7.83 (ddd, J=0.74, 2.37, 9.22 Hz, 1H), 8.43 (d, J=7.51 Hz, 1H), 8.67 (s, 1H). $^{13}$C NMR (101 MHz, CDCl$_3$) δ 15.09, 24.40, 25.39, 32.51, 38.24, 51.52, 114.96, 125.61, 127.66, 130.43, 133.52, 146.47

MS (ESI) m/z 328 [M+H]

4-(bicyclo[2.2.1]heptan-2-ylamino)-N-ethyl-3-nitrobenzenesulfonamide (10)

Following general procedure B, using 4-chloro-N-ethyl-3-nitrobenzenesulfonamide (1 g, 3.78 mmol) and bicyclo[2.2.1]hept-2-ylamine (0.504 g, 4.53 mmol). The reaction was purified by flash-column chromatography on silica gel (50% ethyl acetate in heptane) to afford the desired 4-(bicyclo[2.2.1]heptan-2-ylamino)-N-ethyl-3-nitrobenzenesulfonamide (0.9 g, 2.65 mmol). (Yield: 70.0%)

$^1$H NMR (400 MHz, DMSO-d$_6$) δ 0.99 (t, J=7.22 Hz, 3H), 1.13-1.25 (m, 2H), 1.30-1.41 (m, 2H), 1.44-1.60 (m, 3H), 1.92 (ddd, J=2.33, 7.63, 12.85 Hz, 1H), 2.29-2.34 (m, 2H), 2.77 (qd, J=5.63, 7.21 Hz, 2H), 3.60 (ddd, J=2.51, 5.54, 10.75 Hz, 1H), 7.19 (d, J=9.19 Hz, 1H), 7.55 (t, J=5.71 Hz, 1H), 7.82 (ddd, J=0.66, 2.26, 9.18 Hz, 1H), 8.13 (d, J=6.12 Hz, 1H), 8.43 (d, J=2.23 Hz, 1H). $^{13}$C NMR (101 MHz, DMSO-d$_6$) δ 15.12, 26.17, 28.30, 35.81, 35.86, 37.96, 41.79, 56.05, 116.72, 126.34, 126.89, 130.44, 133.80, 146.17.

MS (ESI) m/z 340 [M+H]

4-(cyclooctylamino)-N-ethyl-3-nitrobenzenesulfonamide (11)

Following general procedure B, using 4-chloro-N-ethyl-3-nitrobenzenesulfonamide (1 g, 3.78 mmol) and cyclooctanamine (0.577 g, 4.53 mmol). The reaction was purified by flash-column chromatography on silica gel (40% ethyl acetate in heptane) to afford the desired 4-(cyclooctylamino)-N-ethyl-3-nitrobenzenesulfonamide (1.1 g, 3.09 mmol). (Yield: 82.0%)

$^1$H NMR (400 MHz, DMSO-d$_6$) δ 0.99 (t, J=7.21 Hz, 3H), 1.52-1.64 (m, 8H), 1.66-1.79 (m, 4H), 1.84-1.92 (m, 2H), 2.77 (qd, J=5.59, 7.19 Hz, 2H), 3.87-3.94 (m, 1H), 7.22 (d, J=9.26 Hz, 1H), 7.54 (t, J=5.69 Hz, 1H), 7.81 (ddd, J=0.66, 2.34, 9.11 Hz, 1H), 8.34 (d, J=7.76 Hz, 1H), 8.43 (d, J=2.25 Hz, 1H). $^{13}$C NMR (101 MHz, DMSO-d$_6$) δ 15.13, 23.48, 25.40, 27.05, 31.70, 37.96, 52.49, 116.54, 126.49, 126.56, 130.11, 133.90, 146.07.

MS (ESI) m/z 356 [M+H]

4-(adamantan-2-ylamino)-N-ethyl-3-nitrobenzenesulfonamide (12)

Following general procedure B, using 4-chloro-N-ethyl-3-nitrobenzenesulfonamide (2.380 g, 8.99 mmol) and adamantan-2-amine hydrochloride (1.688 g, 8.99 mmol). The reaction was purified by flash-column chromatography on silica gel (10% methanol in dichloromethane) to afford the desired 4-(adamantan-2-ylamino)-N-ethyl-3-nitrobenzenesulfonamide (3.05 g, 8.04 mmol). (Yield: 89.0%).

1H NMR (400 MHz, CDCl$_3$) δ 1.04 (t, J=7.23 Hz, 3H), 1.57-2.04 (m, 14H), 2.90 (qd, J=5.77, 7.20 Hz, 2H), 3.79 (dt, J=2.89, 6.46 Hz, 1H), 5.68 (t, J=5.91 Hz, 1H), 6.92 (d, J=9.30 Hz, 1H), 7.76 (ddd, J=0.62, 2.31, 9.13 Hz, 1H), 8.58 (d, J=2.26 Hz, 1H), 8.86 (d, J=7.46 Hz, 1H). $^{13}$C NMR (101 MHz, CDCl$_3$) δ 14.88, 26.96, 31.49, 36.80, 37.21, 38.16, 56.71, 115.24, 125.75, 127.34, 130.25, 133.61, 146.36.

MS (ESI) m/z 380 [M+H]

4-(cyclohexylamino)-N-methyl-3-nitrobenzenesulfonamide (13)

Following general procedure B, using 4-chloro-N-methyl-3-nitrobenzenesulfonamide (1 g, 3.99 mmol) and cyclohexanamine (0.548 ml, 4.79 mmol). The reaction was purified by flash-column chromatography on silica gel (30% ethyl acetate in heptane) to afford the desired 4-(cyclohexylamino)-N-methyl-3-nitrobenzenesulfonamide (0.600 g, 1.915 mmol). (Yield: 48.0%)

$^1$H NMR (400 MHz, DMSO-d$_6$) δ 1.20-1.32 (m, 1H), 1.37-1.47 (m, 4H), 1.56-1.66 (m, 1H), 1.68-1.76 (m, 2H), 1.92-2.01 (m, 2H), 2.41 (s, 3H), 3.62-3.80 (m, 1H), 7.33 (d, J=9.27 Hz, 1H), 7.45 (s, 1H), 7.77 (ddd, J=0.68, 2.29, 9.15 Hz, 1H), 8.29 (d, J=7.74 Hz, 1H), 8.42 (d, J=2.24 Hz, 1H). $^{13}$C NMR (101 MHz, DMSO-d$_6$) δ 24.47, 25.42, 29.06, 32.22, 51.16, 116.50, 125.23, 126.78, 130.07, 133.88, 146.38.

MS (ESI) m/z 314 [M+H]

4-(adamantan-2-ylamino)-N-methyl-3-nitrobenzenesulfonamide (14)

Following general procedure B, using 4-chloro-N-methyl-3-nitrobenzenesulfonamide (1 g, 3.99 mmol) and adamantan-2-amine hydrochloride (0.749 ml, 3.99 mmol). The reaction was purified by flash-column chromatography on silica gel (30% ethyl acetate in heptane) to afford the desired 4-(adamantan-2-ylamino)-N-methyl-3-nitrobenzenesulfonamide (0.670 g, 1.833 mmol). (Yield: 46.0%).

$^1$H NMR (400 MHz, DMSO-d$_6$) δ 1.63-1.71 (m, 2H), 1.73-1.77 (m, 2H), 1.83-1.94 (m, 8H), 2.01-2.07 (m, 2H), 2.41 (s, 3H), 3.96-4.07 (m, 1H), 7.30 (d, J=9.27 Hz, 1H), 7.46 (s, 1H), 7.78 (dd, J=2.26, 9.09 Hz, 1H), 8.44 (d, J=2.25 Hz, 1H), 8.79 (d, J=7.60 Hz, 1H). $^{13}$C NMR (101 MHz, DMSO-d$_6$) δ 26.95, 29.06, 31.39, 31.66, 36.58, 37.26, 56.00, 116.55, 125.44, 126.80, 130.28, 133.98, 146.37.

MS (ESI) m/z 329 [M+H]

N-(tert-butyl)-4-(cyclohexylamino)-3-nitrobenzenesulfonamide (15)

Following general procedure B, using N-(tert-butyl)-4-chloro-3-nitrobenzenesulfonamide (0.950 g, 3.25 mmol) and cyclohexanamine (0.445 ml, 3.89 mmol). The reaction was purified by flash-column chromatography on silica gel (30% ethyl acetate in heptane) to afford the desired N-(tert-butyl)-4-(cyclohexylamino)-3-nitrobenzenesulfonamide (1.08 g, 3.04 mmol). (Yield: 94.0%)

$^1$H NMR (400 MHz, DMSO-d$_6$) δ 1.11 (s, 9H), 1.21-1.31 (m, 1H), 1.35-1.49 (m, 4H), 1.56-1.64 (m, 1H), 1.68-1.76 (m, 2H), 1.92-1.99 (m, 2H), 3.65-3.78 (m, 1H), 7.31 (d, J=9.28 Hz, 1H), 7.51 (s, 1H), 7.83 (ddd, J=0.69, 2.29, 9.21 Hz, 1H), 8.26 (d, J=7.68 Hz, 1H), 8.47 (d, J=2.26 Hz, 1H). $^{13}$C NMR (101 MHz, DMSO-d$_6$) δ 24.50, 25.42, 30.22, 32.25, 51.18, 53.74, 116.33, 125.98, 129.87, 130.50, 133.80, 146.07.

MS (ESI) m/z 356 [M+H]

N-(tert-butyl)-4-(adamantan-2-ylamino)-3-nitrobenzenesulfonamide (16)

Following general procedure B, using N-(tert-butyl)-4-chloro-3-nitrobenzenesulfonamide (1, 3.42 mmol)) and adamantan-2-amine hydrochloride (0.641 g, 3.42 mmol). The reaction was purified by flash-column chromatography on silica gel (50% ethyl acetate in heptane) to afford the desired N-(tert-butyl)-4-(adamantan-2-ylamino)-3-nitrobenzenesulfonamide (1.11 g, 2.72 mmol). (Yield: 80.0%)

$^1$H NMR (400 MHz, DMSO-d$_6$) δ 1.12 (s, 9H), 1.62-1.71 (m, 2H), 1.73-1.77 (m, 2H), 1.81-1.95 (m, 8H), 2.01-2.06 (m, 2H), 3.99-4.02 (m, 1H), 7.28 (d, J=9.28 Hz, 1H), 7.53 (s, 1H), 7.83 (ddd, J=0.64, 2.30, 9.27 Hz, 1H), 8.49 (d, J=2.26 Hz, 1H), 8.77 (d, J=7.58 Hz, 1H). $^{13}$C NMR (101 MHz, DMSO-d$_6$) δ 26.95, 30.23, 31.40, 31.67, 36.59, 37.27, 55.99, 116.37, 125.98, 130.06, 130.71, 133.90, 146.06.

MS (ESI) m/z 408 [M+H]

N-(2-(tert-butoxy)ethyl)-4-(cyclohexylamino)-3-nitrobenzenesulfonamide (17)

Following general procedure B, using N-(2-(tert-butoxy)ethyl)-4-chloro-3-nitrobenzenesulfonamide (1 g, 2.97 mmol) and cyclohexylamine (0.408 ml, 3.56 mmol). The reaction was purified by flash-column chromatography on silica gel (5% methanol in dichloromethane) to afford the desired N-(2-(tert-butoxy)ethyl)-4-(cyclohexylamino)-3-nitrobenzenesulfonamide (0.600 g, 1.502 mmol). (Yield: 50.6%)

$^1$H NMR (400 MHz, DMSO) δ 1.05 (s, 9H), 1.26 (d, J=12.01 Hz, 1H), 1.35-1.51 (m, 4H), 1.61 (d, J=12.00 Hz, 1H), 1.72 (d, J=11.11 Hz, 2H), 1.92-2.02 (m, 2H), 2.84 (t, J=6.05 Hz, 2H), 3.27 (t, J=6.03 Hz, 2H), 3.73 (d, J=9.02 Hz, 1H), 7.32 (d, J=9.28 Hz, 1H), 7.64 (s, 1H), 7.80 (ddd, J=0.70, 2.28, 9.18 Hz, 1H), 8.28 (d, J=7.78 Hz, 1H), 8.43 (d, J=2.22 Hz, 1H). $^{13}$C NMR (101 MHz, MeOD) δ 24.07, 25.15, 26.27, 32.06, 43.33, 51.04, 60.27, 73.01, 115.17, 126.39, 126.55, 130.15, 133.24, 146.20.

N-cyclohexyl-4-((4-methylpiperazin-1-yl)sulfonyl)-2-nitroaniline (18)

Following general procedure B, using 1-((4-chloro-3-nitrophenyl)sulfonyl)-4-methylpiperazine (1.7 g, 5.32 mmol) and cyclohexylamine (0.703 ml, 6.38 mmol). The reaction was purified by flash-column chromatography on silica gel (5% methanol in dichloromethane) to afford the desired N-cyclohexyl-4-(4-methylpiperazin-1-yl)sulfonyl)-2-nitroaniline (1.6 g, 4.18 mmol). (Yield: 79.0%)

$^1$H NMR (400 MHz, DMSO-d$_6$) δ 1.21-1.34 (m, 2H), 1.41-1.49 (m, 3H), 1.57-1.67 (m, 1H), 1.67-1.79 (m, 2H), 1.90-2.03 (m, 2H), 2.15 (s, 3H), 2.36 (t, J=4.92 Hz, 4H), 2.91 (t, J=4.84 Hz, 4H), 3.74 (q, J=6.92, 8.03 Hz, 1H), 7.32 (d, J=9.27 Hz, 1H), 7.72 (ddd, J=0.69, 2.24, 9.28 Hz, 1H), 8.31 (q, J=2.84 Hz, 2H). $^{13}$C NMR (101 MHz, DMSO-d$_6$) δ 24.47, 25.40, 32.17, 45.75, 46.13, 51.26, 53.96, 116.42, 120.67, 127.70, 130.41, 134.35, 146.67.

N-cyclohexyl-4-(morpholinosulfonyl)-2-nitroaniline (19)

Following general procedure B, using the commercially available 4-((4-chloro-3-nitrophenyl)sulfonyl)morpholine (1.0 g, 3.26 mmol) and cyclohexylamine (0.448 ml, 3.91 mmol). The reaction was purified by flash-column chromatography on silica gel (100% EtOAc in heptane) to afford the desired N-cyclohexyl-4-(morpholinosulfonyl)-2-nitroaniline (1.0 g, 2.71 mmol). (Yield: 83.0%)

$^1$H NMR (400 MHz, DMSO-d$_6$) δ 1.17-1.32 (m, 2H), 1.37-1.50 (m, 3H), 1.56-1.66 (m, 1H), 1.67-1.76 (m, 2H), 1.90-2.03 (m, 2H), 2.83-2.94 (m, 4H), 3.59-3.70 (m, 4H), 3.74 (dt, J=6.26, 13.68 Hz, 1H), 7.33 (d, J=9.29 Hz, 1H), 7.72 (ddd, J=0.69, 2.28, 9.23 Hz, 1H), 8.31 (d, J=2.26 Hz, 1H), 8.33 (s, 1H). $^{13}$C NMR (101 MHz, DMSO-d$_6$) δ 24.48, 25.39, 32.17, 46.25, 51.28, 65.73, 116.47, 120.12, 127.89, 130.47, 134.39, 146.76.

3-amino-4-(cyclopropylamino)-N-ethylbenzenesulfonamide (20)

Following general procedure C, using 4-(cyclopropylamino)-N-ethyl-3-nitrobenzenesulfonamide (0.765 g, 2.68 mmol) to afford the desired 3-amino-4-(cyclopropylamino)-N-ethylbenzenesulfonamide (0.500 g, 1.958 mmol). (Yield: 73.0%)

$^1$H NMR (400 MHz, CDCl$_3$) δ 0.43-0.51 (m, 2H), 0.68-0.74 (m, 2H), 0.97 (t, J=7.26 Hz, 3H), 2.31-2.39 (m, 1H), 2.83 (q, J=7.27 Hz, 2H), 3.70 (s, 2H), 4.63 (s, 1H), 4.70 (s, 1H), 6.93 (d, J=8.43 Hz, 1H), 7.14 (d, J=2.21 Hz, 1H), 7.25-7.30 (m, 1H). $^{13}$C NMR (101 MHz, CDCl$_3$) δ 7.25, 14.74, 24.96, 38.16, 110.47, 114.17, 120.54, 126.87, 133.41, 142.25.

t$_R$ 1.34 min, MS (ESI) m/z 256 [M+H] (100%)

3-amino-4-(cyclopentylamino)-N-ethylbenzenesulfonamide (21)

Following general procedure D, using 4-(cyclopentylamino)-N-ethyl-3-nitrobenzenesulfonamide (1 g, 3.19 mmol) to afford the desired 3-amino-4-(cyclopentylamino)-N-ethylbenzenesulfonamide (0.760 g, 2.68 mmol). (Yield: 84.0%)

$^1$H NMR (400 MHz, DMSO-$d_6$) δ 0.96 (t, J=7.23 Hz, 3H), 1.46-1.59 (m, 4H), 1.67-1.73 (m, 2H), 1.93-2.01 (m, 2H), 2.70 (q, J=7.23 Hz, 2H), 3.75-3.80 (m, 1H), 4.97 (s, 2H), 4.98 (s, 1H), 6.49 (d, J=8.04 Hz, 1H), 6.93 (d, J=7.74 Hz, 2H). $^{13}$C NMR (101 MHz, DMSO-$d_6$) δ 15.16, 24.34, 33.00, 37.93, 54.17, 108.87, 111.63, 117.54, 126.77, 135.05, 139.08.

$t_R$ 1.64 min, MS (ESI) m/z 284 [M+H] (100%)

3-amino-4-(cyclohexylamino)-N-ethylbenzenesulfonamide (22)

Following general procedure C, using 4-(cyclohexylamino)-N-ethyl-3-nitrobenzenesulfonamide (1.760 g, 5.38 mmol) The reaction was purified by flash-column chromatography on silica gel (10% methanol in dichloromethane) to afford the desired 3-amino-4-(cyclohexylamino)-N-ethylbenzenesulfonamide (1.412 g, 4.75 mmol). (Yield: 88.0%)

$^1$H NMR (400 MHz, CDCl$_3$) δ 1.10 (t, J=7.23 Hz, 3H), 1.17-1.51 (m, 6H), 1.70 (dt, J=3.81, 12.74 Hz, 1H), 1.75-1.87 (m, 2H), 2.02-2.13 (m, 2H), 2.96 (qd, J=5.93, 7.18 Hz, 2H), 3.33 (tt, J=3.76, 10.20 Hz, 1H), 3.49 (s, 2H), 4.46 (t, J=6.14 Hz, 1H), 6.64 (dd, J=0.60, 8.40 Hz, 1H), 7.22 (d, J=2.18 Hz, 1H), 7.34 (dd, J=2.17, 8.42 Hz, 1H). $^{13}$C NMR (101 MHz, CDCl$_3$) δ 14.99, 24.90, 25.81, 33.16, 38.21, 51.53, 109.71, 115.64, 121.55, 126.26, 132.71, 141.27.

$t_R$ 1.75 min, MS (ESI) m/z 298 [M+H] (100%)

3-amino-4-(bicyclo[2.2.1]heptan-2-ylamino)-N-ethylbenzenesulfonamide (23)

Following general procedure C, using 4-((1S,4S)-bicyclo[2.2.1]heptan-2-ylamino)-N-ethyl-3-nitrobenzenesulfonamide (1.044 g, 3.08 mmol) to afford the desired 3-amino-4-(bicyclo[2.2.1]heptan-2-ylamino)-N-ethylbenzenesulfonamide (0.700 g, 2.262 mmol). (Yield: 73.5%)

$^1$H NMR (400 MHz, DMSO-$d_6$) δ 0.96 (t, J=7.22 Hz, 3H), 1.09-1.15 (m, 2H), 1.21-1.28 (m, 1H), 1.37-1.44 (m, 1H), 1.50 (tp, J=2.79, 3.55, 6.90 Hz, 3H), 1.71-1.77 (m, 1H), 2.20-2.27 (m, 2H), 2.69 (q, J=7.22 Hz, 2H), 3.19-3.25 (m, 1H), 4.85 (d, J=5.64 Hz, 1H), 4.99 (s, 2H), 6.41 (d, J=8.07 Hz, 1H), 6.92 (d, J=2.28 Hz, 1H), 6.94 (d, J=2.20 Hz, 1H). $^{13}$C NMR (101 MHz, DMSO-$d_6$) δ 15.14, 21.23, 26.30, 28.70, 35.49, 35.51, 37.91, 56.30, 108.82, 111.57, 117.45, 126.85, 135.06, 138.51.

$t_R$ 1.83 min, MS (ESI) m/z 310 [M+H] (94%)

3-amino-4-(cyclooctylamino)-N-ethylbenzenesulfonamide (24)

Following general procedure C, using 4-(cyclooctylamino)-N-ethyl-3-nitrobenzenesulfonamide (1.1 g, 3.09 mmol) to afford the desired 3-amino-4-(cyclooctylamino)-N-ethylbenzenesulfonamide (0.700 g, 2.151 mmol). (Yield: 69.5%)

$^1$H NMR (400 MHz, DMSO-$d_6$) δ 0.96 (t, J=7.20 Hz, 3H), 1.42-1.83 (m, 15H), 2.69 (q, J=7.21 Hz, 2H), 3.51 (qt, J=3.41, 7.64 Hz, 1H), 4.83 (d, J=7.39 Hz, 1H), 4.96 (s, 2H), 6.37-6.42 (m, 1H), 6.91-6.96 (m, 2H). $^{13}$C NMR (101 MHz, DMSO-$d_6$) δ 15.14, 24.07, 25.89, 27.18, 32.09, 37.91, 60.23, 108.56, 111.93, 117.67, 126.44, 135.05, 138.33.

$t_R$ 1.98 min, MS (ESI) m/z 326 [M+H] (100%)

4-(adamantan-2-ylamino)-3-amino-N-ethylbenzenesulfonamide (25)

Following general procedure C, using 4-(adamantan-2-ylamino)-N-ethyl-3-nitrobenzenesulfonamide (3.05 g, 8.04 mmol). The reaction was purified by flash-column chromatography on silica gel (10% methanol in dichloromethane) to afford the desired 4-(adamantan-2-ylamino)-3-amino-N-ethylbenzenesulfonamide (1.2 g, 3.43 mmol). (Yield: 42.7%)

$^1$H NMR (400 MHz, CDCl$_3$) δ 1.12 (t, J=7.24 Hz, 3H), 1.61-2.12 (m, 15H), 2.98 (qd, J=6.10, 7.26 Hz, 2H), 3.37 (s, 2H), 3.63 (s, 1H), 4.29 (t, J=6.09 Hz, 1H), 6.59 (dd, J=0.68, 8.43 Hz, 1H), 7.23 (d, J=2.17 Hz, 1H), 7.35 (dd, J=2.17, 8.42 Hz, 1H). $^{13}$C NMR (101 MHz, CDCl$_3$) δ 15.03, 27.25, 31.59, 37.24, 37.57, 38.21, 56.49, 109.47, 115.80, 121.80, 126.02, 132.63, 141.71.

$t_R$ 2.05, MS (ESI) m/z 350 [M+H] (83%)

3-amino-4-(cyclohexylamino)-N-methylbenzenesulfonamide (26)

Following general procedure C, using 4-(cyclohexylamino)-N-methyl-3-nitrobenzenesulfonamide (0.600 g, 1.915 mmol) to afford the desired 3-amino-4-(cyclohexylamino)-N-methylbenzenesulfonamide (0.523 g, 1.846 mmol). (Yield: 96.0%)

$^1$H NMR (400 MHz, DMSO-$d_6$) δ 1.14-1.27 (m, 3H), 1.29-1.42 (m, 2H), 1.58-1.67 (m, 1H), 1.69-1.78 (m, 2H), 1.93-2.00 (m, 2H), 2.34 (s, 3H), 3.23-3.35 (m, 1H), 4.85 (d, J=7.45 Hz, 1H), 4.95 (s, 2H), 6.42-6.57 (m, 1H), 6.91 (d, J=7.04 Hz, 2H). $^{13}$C NMR (101 MHz, DMSO-$d_6$) δ 25.16, 26.05, 29.20, 33.05, 51.19, 108.37, 112.14, 117.88, 125.18, 134.94, 138&.61.

$t_R$ 1.67 min, MS (ESI) m/z 284 [M+H] (100%)

3-amino-4-(adamantan-2-ylamine)-N-methylbenzenesulfonamide (27)

Following general procedure C using 4-(adamantan-2-ylamino)-N-methyl-3-nitrobenzenesulfonamide (0.67 g, 1.833 mmol) to afford the desired 3-amino-4-(adamantan-2-ylamine)-N-methylbenzenesulfonamide (0.550 g, 1.640 mmol). (Yield: 89.0%)

$^1$H NMR (400 MHz, DMSO-$d_6$) δ 1.46-1.56 (m, 2H), 1.67-1.75 (m, 3H), 1.78-1.90 (m, 6H), 1.95-2.00 (m, 2H), 2.05-2.12 (m, 2H), 2.34 (s, 3H), 3.55-3.61 (m, 1H), 4.72 (d, J=6.33 Hz, 1H), 5.06 (s, 2H), 6.46 (d, J=8.39 Hz, 1H), 6.93 (dd, J=2.24, 8.33 Hz, 1H), 6.97 (d, J=2.18 Hz, 1H). $^{13}$C NMR (101 MHz, DMSO-$d_6$) δ 27.27, 29.20, 31.33, 37.21, 37.68, 56.48, 108.72, 112.62, 118.05, 125.56, 135.29, 138.92.

$t_R$ 1.97 min, MS (ESI) m/z 336 [M+H] (100%)

3-amino-N-(tert-butyl)-4-(cyclohexylamino)benzenesulfonamide (28)

Following general procedure C, using N-(tert-butyl)-4-(cyclohexylamino)-3-nitrobenzenesulfonamide (1.05 g, 2.95 mmol) to afford the desired 3-amino-N-(tert-butyl)-4-(cyclohexylamino)benzenesulfonamide (0.850 g, 2.61 mmol). (Yield: 88.0%)

$^1$H NMR (400 MHz, DMSO-$d_6$) δ 1.07 (s, 9H), 1.12-1.25 (m, 3H), 1.29-1.41 (m, 2H), 1.63 (t, J=3.78, 12.66 Hz, 1H), 1.68-1.79 (m, 2H), 1.91-2.01 (m, 2H), 3.22-3.32 (m, 1H), 4.78 (d, J=7.47 Hz, 1H), 4.89 (s, 2H), 6.43-6.53 (m, 1H), 6.90 (s, 1H), 6.94-6.99 (m, 2H). $^{13}$C NMR (101 MHz, DMSO-d$_6$) δ 25.18, 26.07, 30.21, 33.07, 51.23, 53.07, 108.35, 112.15, 117.63, 130.44, 134.69, 138.19.

t$_R$ 1.93 min, MS (ESI) m/z 326 [M+H] (100%)

3-amino-N-(tert-butyl)-4-(adamantan-2-ylamino)benzenesulfonamide (29)

Following general procedure C, using N-(tert-butyl)-4-(adamantan-2-ylamino)-3-nitrobenzenesulfonamide (1.11 g, 2.72 mmol) to afford the desired 3-amino-N-(tert-butyl)-4-(adamantan-2-ylamine)benzenesulfonamide (0.917 g, 2.429 mmol). (Yield: 89.0%)

$^1$H NMR (400 MHz, DMSO-d$_6$) δ 1.08 (s, 9H), 1.45-1.56 (m, 2H), 1.70-1.75 (m, 2H), 1.82-1.91 (m, 6H), 1.95-2.02 (m, 2H), 2.03-2.14 (m, 2H), 3.52-3.60 (m, 1H), 4.66 (d, J=6.26 Hz, 1H), 5.01 (s, 2H), 6.44 (d, J=8.41 Hz, 1H), 6.93 (s, 1H), 6.98 (dd, J=2.24, 8.32 Hz, 1H), 7.01 (d, J=2.22 Hz, 1H). $^{13}$C NMR (101 MHz, DMSO-d$_6$) δ 27.28, 27.46, 30.23, 31.37, 37.22, 37.70, 56.51, 108.64, 112.62, 117.80, 130.82, 135.01, 138.53.

t$_R$ 2.22 min, MS (ESI) m/z 378 [M+H] (100%)

3-amino-N-(2-(tert-butoxy)ethyl)-4-(cyclohexylamino)benzenesulfonamide (30)

Following general procedure C, using N-(2-(tert-butoxy)ethyl)-4-(cyclohexylamino)-3-nitrobenzenesulfonamide (0.600 g, 1.502 mmol) The reaction was purified by flash-column chromatography on silica gel (10% methanol in dichloromethane) to afford the desired 3-amino-N-(2-(tert-butoxy)ethyl)-4-(cyclohexylamino)benzenesulfonamide (0.400 g, 1.082 mmol). (Yield: 72.1%)

$^1$H NMR (400 MHz, DMSO-d$_6$) δ 1.07 (s, 9H), 1.14-1.27 (m, 4H), 1.31-1.36 (m, 1H), 1.38 (s, 2H), 1.55-1.67 (m, 1H), 1.70-1.78 (m, 2H), 1.91-2.02 (m, 2H), 2.73 (td, J=2.85, 6.66 Hz, 2H), 3.23 (td, J=4.87, 6.64 Hz, 3H), 4.78-4.90 (m, 1H), 4.94 (s, 1H), 6.22-6.30 (m, 1H), 6.50 (dd, J=3.56, 8.97 Hz, 1H), 6.90-6.95 (m, 1H). $^{13}$C NMR (101 MHz, MeOD) δ 25.69, 25.94, 26.43, 32.70, 43.32, 51.27, 60.28, 73.05, 83.03, 102.34, 102.77, 108.65, 113.54, 119.52, 119.99, 124.63, 125.78, 133.69, 140.12.

t$_R$ 2.23 min, MS (ESI) m/z 370 [M+H] (80%)

N1-cyclohexyl-4-((4-methylpiperazin-1-yl)sulfonyl)benzene-1,2-diamine (31)

Following general procedure C, using N-cyclohexyl-4-(4-methylpiperazin-1-yl)sulfonyl)-2-nitroaniline (1.6 g, 4.18 mmol). The reaction was purified by flash-column chromatography on silica gel (10% methanol in dichloromethane) to afford the desired N1-cyclohexyl-4-((4-methylpiperazin-1-yl)sulfonyl)benzene-1,2-diamine (0.850 g, 2.411 mmol). (Yield: 57.6%)

$^1$H NMR (400 MHz, Acetone-d$_6$) δ 1.19-1.34 (m, 3H), 1.36-1.49 (m, 2H), 1.62-1.70 (m, 1H), 1.73-1.84 (m, 2H), 2.08-2.11 (m, 2H), 2.17 (s, 3H), 2.38 (t, J=4.97 Hz, 4H), 2.81-2.99 (m, 4H), 3.40 (dtt, J=3.66, 7.41, 10.66 Hz, 1H), 4.46 (s, 2H), 4.50 (d, J=7.51 Hz, 1H), 6.69 (d, J=8.92 Hz, 1H), 7.04-7.09 (m, 2H). $^{13}$C NMR (101 MHz, Acetone-d$_6$) δ 24.84, 25.77, 32.89, 45.15, 46.08, 51.21, 54.08, 108.50, 114.09, 120.14, 121.46, 134.22, 140.09.

t$_R$ 1.30 min, MS (ESI) m/z 353 [M+H] (100%)

N1-cyclohexyl-4-(morpholinosulfonyl)benzene-1,2-diamine (32)

Following general procedure C, using N-cyclohexyl-4-(morpholinosulfonyl)-2-nitroaniline (1 g, 2.71 mmol). The reaction was purified by flash-column chromatography on silica gel (10% methanol in dichloromethane) to afford the desired N1-cyclohexyl-4-(morpholinosulfonyl)benzene-1,2-diamine (0.612 g, 1.803 mmol). (Yield: 66.6%)

$^1$H NMR (400 MHz, Acetone-d$_6$) δ 1.23-1.34 (m, 3H), 1.37-1.52 (m, 2H), 1.62-1.72 (m, 1H), 1.74-1.84 (m, 2H), 2.08-2.12 (m, 2H), 2.81-2.90 (m, 4H), 3.29-3.50 (m, 1H), 3.61-3.69 (m, 4H), 4.49 (s, 2H), 4.54 (d, J=7.50 Hz, 1H), 6.70 (d, J=8.88 Hz, 1H), 7.03-7.09 (m, 2H). $^{13}$C NMR (101 MHz, Acetone-d$_6$) δ 24.83, 25.75, 32.88, 46.27, 51.21, 65.78, 108.49, 114.04, 120.22, 120.95, 134.28, 140.20.

t$_R$ 1.79 min, MS (ESI) m/z 340 [M+H] (100%)

3-(benzylamino)-4-(cyclopropylamino)-N-ethylbenzenesulfonamide (33)

Following general procedure D using 3-amino-4-(cyclopropylamino)-N-ethylbenzenesulfonamide (0.200 g, 0.783 mmol) and benzylbromide (0.094 ml, 0.783 mmol). The residue was purified by flash-column chromatography (35% ethyl acetate in heptane) on silica gel to afford the desired 3-(benzylamino)-4-(cyclopropylamino)-N-ethylbenzenesulfonamide (0.120 g, 0.347 mmol). (Yield: 44.3%)

$^1$H NMR (400 MHz, DMSO-d$_6$) δ 0.43-0.50 (m, 2H), 0.73-0.81 (m, 2H), 0.83-0.90 (m, 3H), 2.41-2.50 (m, 3H), 4.31 (d, J=2.94 Hz, 2H), 5.51 (s, 1H), 5.91 (s, 1H), 6.71 (d, J=2.11 Hz, 1H), 6.88 (dd, J=7.06, 12.41 Hz, 2H), 7.00 (dd, J=2.06, 8.24 Hz, 1H), 7.21-7.27 (m, 1H), 7.32-7.38 (m, 4H). $^{13}$C NMR (101 MHz, CDCl$_3$) δ 7.34, 14.95, 25.11, 38.18, 48.75, 110.68, 120.18, 127.57, 128.11, 128.69, 135.29, 138.40, 142.23.

t$_R$ 1.85, MS (ESI) m/z 346 [M+H] (87%)

4-(cyclopropylamino)-N-ethyl-3-((pyridin-4-ylmethyl)amino)benzenesulfonamide (34)

Following general procedure D, using 3-amino-4-(cyclopropylamino)-N-ethylbenzenesulfonamide (0.250 g, 0.979 mmol) and 4-(bromomethyl)pyridine hydrobromide (0.867 g, 3.43 mmol). The residue was purified by flash-column chromatography (100% ethyl acetate) on silica gel to afford the 4-(cyclopropylamino)-N-ethyl-3-((pyridin-4-ylmethyl)amino)benzenesulfonamide (0.0139 g, 0.040 mmol). (Yield: 4.10%)

$^1$H NMR (400 MHz, DMSO-d$_6$) δ 0.44-0.54 (m, 2H), 0.76-0.80 (m, 3H), 0.83 (t, J=7.22 Hz, 2H), 2.41-2.49 (m, 3H), 4.39 (d, J=5.08 Hz, 2H), 5.67 (t, J=5.63 Hz, 1H), 5.90 (d, J=1.94 Hz, 1H), 6.58 (d, J=2.06 Hz, 1H), 6.87-6.93 (m, 2H), 7.02 (dd, J=2.02, 8.23 Hz, 1H), 7.37-7.40 (m, 2H), 8.51-8.54 (m, 2H). $^{13}$C NMR (101 MHz, MeOD) δ 6.35, 13.08, 13.65, 19.48, 24.51, 37.42, 45.99, 60.14, 108.30, 109.56, 118.33, 122.92, 127.24, 134.25, 141.14, 147.83, 171.59. MS (ESI) m/z 347 t$_R$ 1.25, MS (ESI) m/z 347 [M+H] (87%)

3-(benzylamino)-4-(cyclopentylamino)-N-ethylbenzenesulfonamide (35)

Following general procedure D, using 3-amino-4-(cyclopentylamino)-N-ethylbenzenesulfonamide (0.250 g, 0.882 mmol) and benzylbromide (0.106 ml, 0.882 mmol). The residue was purified by flash-column chromatography (30% ethyl acetate in heptane) on silica gel to afford the desired 3-(benzylamino)-4-(cyclopentylamino)-N-ethylbenzenesulfonamide (0.0608 g, 0.163 mmol). (Yield: 18.5%)

$^1$H NMR (400 MHz, DMSO-d$_6$) δ 0.85 (t, J=7.26 Hz, 3H), 1.45-1.66 (m, 4H), 1.65-1.77 (m, 2H), 1.92-2.05 (m, 2H), 2.46 (d, J=8.07 Hz, 2H), 3.82 (p, J=5.97 Hz, 1H), 4.33 (s, 2H), 5.12 (s, 1H), 5.90 (s, 1H), 6.54 (d, J=8.38 Hz, 1H), 6.69 (d, J=2.10 Hz, 1H), 6.83-6.91 (m, 1H), 6.97 (dd, J=2.09, 8.28 Hz, 1H), 7.20-7.28 (m, 1H), 7.31-7.38 (m, 4H). $^{13}$C NMR (101 MHz, CDCl$_3$) δ 14.92, 24.21, 32.99, 38.16, 49.18, 55.51, 112.41, 112.99, 121.02, 127.76, 128.07, 128.40, 128.69, 134.11, 137.19, 139.86.

$t_R$ 2.02, MS (ESI) m/z 374 [M+H] (64%)

4-(cyclopentylamino)-N-ethyl-3-((pyridin-4-ylmethyl)amino)benzenesulfonamide (36)

Following general procedure D using 3-amino-4-(cyclopentylamino)-N-ethylbenzenesulfonamide (0.250 g, 0.882 mmol) and 4-(bromomethyl)pyridine hydrobromide (0.781 g, 3.09 mmol). The residue was purified by flash-column chromatography (100% ethyl acetate) on silica gel to afford the 4-(cyclopentylamino)-N-ethyl-3-((pyridin-4-ylmethyl)amino)benzenesulfonamide (0.0475 g, 0.127 mmol). (Yield: 14.9%)

$^1$H NMR (400 MHz, DMSO-d$_6$) δ 0.81 (t, J=7.23 Hz, 3H), 1.48-1.63 (m, 5H), 1.68-1.78 (m, 2H), 1.97-2.08 (m, 2H), 2.43 (qd, J=5.73, 7.23 Hz, 2H), 3.83 (s, 1H), 4.35-4.49 (m, 2H), 5.22 (s, 1H), 5.88 (t, J=5.36 Hz, 1H), 6.52-6.59 (m, 1H), 6.87 (t, J=5.82 Hz, 1H), 6.98 (dd, J=2.05, 8.31 Hz, 1H), 7.33-7.42 (m, 2H), 8.51-8.54 (m, 2H). $^{13}$C NMR (101 MHz, CDCl$_3$) δ 14.86, 24.27, 33.52, 38.07, 47.19, 54.51, 110.09, 110.45, 120.46, 122.67, 127.06, 134.80, 141.41, 149.40.

$t_R$ 1.44 min, MS (ESI) m/z 375 [M+H] (100%)

3-(benzylamino)-4-(cyclohexylamino)-N-ethylbenzenesulfonamide (37)

Following general procedure D, using 3-amino-4-(cyclohexylamino)-N-ethylbenzenesulfonamide (0.200 g, 0.672 mmol) and benzylbromide (0.080 ml, 0.672 mmol). The residue was purified by flash-column chromatography (85% methanol in water) on silica gel to afford the desired 3-(benzylamino)-4-(cyclohexylamino)-N-ethylbenzenesulfonamide (0.0403 g, 0.104 mmol). (Yield: 15.5%)

$^1$H NMR (400 MHz, CDCl$_3$) δ 1.04 (t, J=7.23 Hz, 3H), 1.19-1.50 (m, 5H), 1.67-1.75 (m, 1H), 1.76-1.85 (m, 2H), 2.03-2.15 (m, 2H), 2.85 (qd, J=6.08, 7.23 Hz, 2H), 3.27-3.43 (m, 2H), 3.83 (d, J=6.24 Hz, 1H), 4.20 (t, J=6.14 Hz, 1H), 4.32 (d, J=5.42 Hz, 2H), 6.67 (dd, J=0.66, 8.33 Hz, 1H), 7.15 (d, J=2.11 Hz, 1H), 7.30-7.44 (m, 6H). $^{13}$C NMR (101 MHz, CDCl$_3$) δ 14.98, 24.96, 25.84, 33.29, 38.16, 48.96, 51.57, 109.40, 111.52, 120.64, 126.77, 127.53, 128.02, 128.71, 135.30, 138.62, 141.09.

$t_R$ 2.14 min, MS (ESI) m/z 388 [M+H] (100%)

4-(cyclohexylamino)-N-ethyl-3-((pyridin-4-ylmethyl)amino)benzenesulfonamide (38)

Following general procedure D, using 3-amino-4-(cyclohexylamino)-N-ethylbenzenesulfonamide (0.200 g, 0.672 mmol) and 4-(bromomethyl)pyridinehydrobromide (0.340 g, 1.345 mmol). The residue was purified by flash-column chromatography (95% ethyl acetate in heptane) on silica gel to afford the desired 4-(cyclohexylamino)-N-ethyl-3-((pyridin-4-ylmethyl)amino)benzenesulfonamide (0.0371 g, 0.095 mmol). (Yield: 14.2%)

$^1$H NMR (400 MHz, CDCl$_3$) δ 1.00 (t, J=7.24 Hz, 3H), 1.20-1.34 (m, 3H), 1.37-1.50 (m, 2H), 1.67-1.75 (m, 2H), 1.77-1.87 (m, 2H), 2.06-2.14 (m, 2H), 2.80 (qd, J=6.04, 7.25 Hz, 2H), 3.29-3.41 (m, 1H), 3.61 (t, J=5.77 Hz, 1H), 3.91 (d, J=6.27 Hz, 1H), 4.32-4.42 (m, 3H), 6.65-6.72 (m, 1H), 7.02 (d, J=2.04 Hz, 1H), 7.27-7.31 (m, 2H), 7.36 (dd, J=2.08, 8.38 Hz, 1H), 8.53-8.60 (m, 2H). $^{13}$C NMR (101 MHz, CDCl$_3$) δ 14.93, 24.91, 25.81, 33.28, 38.09, 47.51, 51.59, 109.79, 111.63, 120.97, 122.54, 126.95, 134.52, 141.13, 147.81, 150.03.

$t_R$ 1.51 min, MS (ESI) m/z 389 [M+H] (100%)

4-(cyclohexylamino)-N-ethyl-3-((pyrimidin-5-ylmethyl)amino)benzenesulfonamide (39)

Following general procedure D, using 3-amino-4-(cyclohexylamino)-N-ethylbenzenesulfonamide (0.150 g, 0.504 mmol) and 5-(chloromethyl)pyrimidine hydrochloride (0.125, 0.757 mmol). The residue was purified by flash-column chromatography (95% ethyl acetate in heptane) on silica gel to afford the desired 4-(cyclohexylamino)-N-ethyl-3-((pyrimidin-5-ylmethyl)amino)benzenesulfonamide (0.120 g, 0.308 mmol). (Yield: 61.1%)

$^1$H NMR (400 MHz, DMSO-d$_6$) δ 0.87 (t, J=7.23 Hz, 3H), 1.16-1.28 (m, 4H), 1.29-1.44 (m, 2H), 1.57-1.67 (m, 1H), 1.70-1.80 (m, 2H), 1.93-2.03 (m, 2H), 2.52-2.58 (m, 2H), 4.36 (d, J=4.67 Hz, 2H), 5.06 (d, J=7.24 Hz, 1H), 5.61 (t, J=5.43 Hz, 1H), 6.57 (d, J=8.47 Hz, 1H), 6.75 (d, J=2.09 Hz, 1H), 6.96 (t, J=5.80 Hz, 1H), 7.02 (dd, J=2.05, 8.38 Hz, 1H), 8.80 (s, 2H), 9.10 (s, 1H). $^{13}$C NMR (101 MHz, MeOD) δ 13.69, 24.82, 25.65, 32.68, 37.52, 42.65, 51.37, 108.42, 109.47, 119.38, 125.79, 133.53, 133.91, 140.23, 156.34, 156.54.

$t_R$ 1.79 min, MS (ESI) m/z 390 [M+H] (91%)

3-(benzylamino)-4-(bicyclo[2.2.1]heptan-2-ylamino)-N-ethylbenzenesulfonamide (40)

Following general procedure D, using 3-amino-4-(bicyclo[2.2.1]heptan-2-ylamino)-N-ethylbenzenesulfonamide (0.200 g, 0.646 mmol) and benzylbromide (0.077 ml, 0.646 mmol). The residue was purified by flash-column chromatography (35% ethyl acetate in heptane) on silica gel to afford the desired 3-(benzylamino)-4-(bicyclo[2.2.1]heptan-2-ylamino)-N-ethylbenzenesulfonamide (0.0525 g, 0.131 mmol). (Yield: 20.3%)

$^1$H NMR (400 MHz, DMSO-d$_6$) δ 0.85 (t, J=7.22 Hz, 3H), 1.12-1.18 (m, 2H), 1.22-1.30 (m, 1H), 1.37-1.57 (m, 4H), 1.71-1.81 (m, 1H), 2.26 (q, J=4.05 Hz, 2H), 2.43-2.49 (m, 2H), 3.22-3.29 (m, 1H), 4.33 (s, 2H), 5.12 (s, 1H), 5.76 (s, 1H), 6.44 (d, J=8.37 Hz, 1H), 6.69 (d, J=2.11 Hz, 1H), 6.87 (t, J=5.86 Hz, 1H), 6.96 (dd, J=2.08, 8.29 Hz, 1H), 7.21-7.27 (m, 1H), 7.30-7.39 (m, 4H). $^{13}$C NMR (101 MHz, CDCl$_3$) δ 14.94, 26.41, 28.44, 35.56, 35.73, 38.16, 40.80, 41.33, 48.88, 56.70, 110.21, 111.20, 120.53, 127.25, 127.54, 128.10, 128.69, 135.25, 138.41, 141.09.

$t_R$ 2.13 min, MS (ESI) m/z 400 [M+H] (100%)

4-(bicyclo[2.2.1]heptan-2-ylamino)-N-ethyl-3-((pyridin-4-ylmethyl)amino) benzenesulfonamide (41)

Following general procedure D, using 3-amino-4-(bicyclo[2.2.1]heptan-2-ylamino)-N-ethylbenzenesulfonamide (0.200 g, 0.646 mmol) and 4-(bromomethyl)pyridine hydrobromide (0.572 g, 2.262 mmol). The residue was purified by flash-column chromatography (100% ethyl acetate) on silica gel to afford the 4-(bicyclo[2.2.1]heptan-2-ylamino)-N-ethyl-3-((pyridin-4-ylmethyl)amino)benzenesulfonamide (0.0582 g, 0.145 mmol). (Yield: 22.5%)

$^1$H NMR (400 MHz, DMSO-d$_6$) δ 0.81 (t, J=7.23 Hz, 3H), 1.13-1.21 (m, 2H), 1.22-1.33 (m, 1H), 1.39-1.61 (m, 4H), 1.72-1.83 (m, 1H), 2.24-2.32 (m, 2H), 2.43 (qd, J=5.73, 7.23 Hz, 2H), 3.29 (s, 1H), 4.33-4.47 (m, 2H), 5.12 (d, J=5.49 Hz, 1H), 5.92 (s, 1H), 6.47 (d, J=8.35 Hz, 1H), 6.55 (d, J=2.11 Hz, 1H), 6.88 (t, J=5.81 Hz, 1H), 6.98 (dd, J=2.04, 8.32 Hz, 1H), 7.36-7.42 (m, 2H), 8.49-8.56 (m, 2H). $^{13}$C NMR (101 MHz, CDCl$_3$) δ 14.82, 26.38, 28.43, 35.55, 35.71, 38.05, 40.71, 41.30, 47.11, 56.65, 109.97, 110.27, 120.31, 122.66, 126.96, 134.80, 140.88, 148.52, 149.47.

$t_R$ 1.53 min, MS (ESI) m/z 401 [M+H] (100%)

3-(benzylamino)-4-(cyclooctylamino)-N-ethylbenzenesulfonamide (42)

Following general procedure D, using 3-amino-4-(cyclooctylamino)-N-ethylbenzenesulfonamide (200 mg, 0.614 mmol) and benzylbromide (0.073 ml, 0.614 mmol). The residue was purified by flash-column chromatography (40% ethyl acetate in heptane) on silica gel to afford the desired 3-(benzylamino)-4-(cyclooctylamino)-N-ethylbenzenesulfonamide (0.0729 g, 0.175 mmol). (Yield: 25.8%)

$^1$H NMR (400 MHz, DMSO-d$_6$) δ 0.85 (t, J=7.23 Hz, 3H), 1.47-1.88 (m, 14H), 2.44 (qd, J=5.77, 7.32 Hz, 2H), 3.55 (s, 1H), 4.33 (s, 2H), 5.09 (s, 1H), 5.68-5.80 (m, 1H), 6.44 (d, J=8.44 Hz, 1H), 6.69 (d, J=2.12 Hz, 1H), 6.85 (t, J=5.85 Hz, 1H), 6.96 (dd, J=2.10, 8.29 Hz, 1H), 7.21-7.39 (m, 5H). $^{13}$C NMR (101 MHz, CDCl$_3$) δ 14.97, 24.10, 25.95, 26.93, 32.68, 38.16, 48.90, 52.90, 110.16, 111.61, 120.54, 127.51, 128.01, 128.69, 135.45, 138.49, 140.51.

$t_R$ 2.24 min, MS (ESI) m/z 416 [M+H] (100%)

4-(cyclooctylamino)-N-ethyl-3-((pyridin-4-ylmethyl)amino)benzenesulfonamide (43)

Following general procedure D, using 3-amino-4-(cyclooctylamino)-N-ethylbenzenesulfonamide (0.200 g, 0.614 mmol) and 4-(bromomethyl)pyridine hydrobromide (0.544 g, 2.151 mmol). The residue was purified by flash-column chromatography (100% ethyl acetate) on silica gel to afford the 4-(cyclooctylamino)-N-ethyl-3-((pyridin-4-ylmethyl)amino)benzenesulfonamide (0.0583 g, 0.140 mmol). (Yield: 22.8%)

$^1$H NMR (400 MHz, DMSO-d$_6$) δ 0.81 (t, J=7.23 Hz, 3H), 1.49-1.90 (m, 14H), 2.34-2.50 (m, 2H), 3.57 (s, 1H), 4.41 (d, J=5.09 Hz, 2H), 5.08 (d, J=7.03 Hz, 1H), 5.89 (t, J=5.74 Hz, 1H), 6.47 (d, J=8.42 Hz, 1H), 6.56 (d, J=2.09 Hz, 1H), 6.86 (t, J=5.83 Hz, 1H), 6.98 (dd, J=2.08, 8.31 Hz, 1H), 7.32-7.43 (m, 2H), 8.48-8.57 (m, 2H). $^{13}$C NMR (101 MHz, CDCl$_3$) δ 14.87, 24.09, 25.93, 26.95, 32.72, 38.07, 47.31, 52.58, 109.69, 111.10, 120.79, 122.68, 126.69, 134.62, 140.86, 148.60, 149.42.

MS (ESI) m/z 417 [M+H] (95%)

4-(adamantan-2-ylamino)-3-(benzylamino)-N-ethylbenzenesulfonamide (44)

Following general procedure D, using 4-(adamantan-2-ylamino)-3-amino-N-ethylbenzenesulfonamide (0.200 g, 0.572 mmol) and benzylbromide (0.082 ml, 0.687 mmol). The residue was purified by flash-column chromatography (10% methanol in dichloromethane) on silica gel to afford the desired 4-(adamantan-2-ylamino)-3-(benzylamino)-N-ethylbenzenesulfonamide (0.0723 g, 0.164 mmol). (Yield: 28.7%)

$^1$H NMR (400 MHz, CDCl$_3$) δ 1.03 (t, J=7.22 Hz, 3H), 1.62-1.83 (m, 6H), 1.92-2.09 (m, 9H), 2.82 (qd, J=5.88, 7.15 Hz, 2H), 3.46 (t, J=5.83 Hz, 1H), 3.64 (dt, J=2.73, 5.96 Hz, 1H), 4.35 (d, J=5.96 Hz, 2H), 4.40 (d, J=6.08 Hz, 1H), 6.62 (d, J=8.43 Hz, 1H), 7.17 (d, J=2.08 Hz, 1H), 7.28-7.33 (m, 1H), 7.35-7.43 (m, 5H). $^{13}$C NMR (101 MHz, CDCl$_3$) δ 14.95, 27.27, 31.62, 37.25, 37.58, 38.15, 49.01, 56.57, 109.31, 112.49, 121.07, 126.50, 127.41, 127.72, 128.69, 135.17, 138.80, 141.61.

$t_R$ 2.50 min, MS (ESI) m/z 440 [M+H] (100%)

4-(adamantan-2-ylamino)-N-ethyl-3-((pyridin-4-ylmethyl)amino)benzenesulfonamide (45)

Following general procedure D, using 4-(adamantan-2-ylamino)-3-amino-N-ethylbenzenesulfonamide (0.200 g, 0.572 mmol and 4-(bromomethyl)pyridinehydrobromide (0.217 g, 0.858 mmol). The residue was purified by flash-column chromatography (40% ethyl acetate in heptane) on silica gel to afford the desired 4-(adamantan-2-ylamino)-N-ethyl-3-((pyridin-4-ylmethyl)amino)benzenesulfonamide (0.0483 g, 0.110 mmol). (Yield: 19.2%)

$^1$H NMR (400 MHz, CDCl$_3$) δ 0.99 (t, J=7.23 Hz, 3H), 1.62-2.12 (m, 15H), 2.78 (qd, J=5.97, 7.22 Hz, 2H), 3.64 (d, J=2.82 Hz, 2H), 4.39 (s, 2H), 4.44 (t, J=6.08 Hz, 1H), 6.64 (d, J=8.87 Hz, 1H), 7.05 (d, J=2.09 Hz, 1H), 7.29-7.32 (m, 2H), 7.37 (dd, J=2.09, 8.39 Hz, 1H), 8.53-8.60 (m, 2H). $^{13}$C NMR (101 MHz, CDCl$_3$) δ 14.91, 31.62, 31.85, 37.22, 37.53, 38.07, 47.59, 56.58, 109.67, 112.49, 121.42, 122.40, 126.70, 134.34, 141.61, 147.99, 149.99.

$t_R$ 1.75 min, MS (ESI) m/z 441 [M+H] (100%)

4-(adamantan-2-ylamino)-N-ethyl-3-((pyrimidin-5-ylmethyl)amino)benzenesulfonamide (46)

Following general procedure D, using 4-(adamantan-2-ylamino)-3-amino-N-ethylbenzenesulfonamide (0.150 g, 0.429 mmol and 5-(chloromethyl)pyrimidinehydrochloride (0.142 g, 0.858 mmol). The residue was purified by flash-column chromatography (100% ethyl acetate in heptane) on silica gel to afford the desired 4-(adamantan-2-ylamino)-N-ethyl-3-((pyrimidin-5-ylmethyl)amino)benzenesulfonamide (0.0312 g, 0.071 mmol). (Yield: 16.42%)

$^1$H NMR (400 MHz, DMSO-d$_6$) δ 0.86 (t, J=7.23 Hz, 3H), 1.53 (d, J=12.31 Hz, 2H), 1.73 (d, J=3.25 Hz, 2H), 1.83 (s, 2H), 1.87 (d, J=3.30 Hz, 4H), 2.02 (s, 2H), 2.09 (d, J=12.92 Hz, 2H), 2.43-2.51 (m, 2H), 3.59-3.67 (m, 1H), 4.41 (d, J=5.35 Hz, 2H), 4.92 (d, J=5.85 Hz, 1H), 5.92 (t, J=5.59 Hz, 1H), 6.54 (d, J=8.49 Hz, 1H), 6.76 (d, J=2.09 Hz, 1H), 6.96 (t, J=5.83 Hz, 1H), 7.02 (dd, J=2.07, 8.38 Hz, 1H), 8.80 (s, 2H), 9.09 (s, 1H).

$^{13}$C NMR (101 MHz, MeOD) δ 13.08, 27.45, 27.58, 31.24, 31.44, 36.92, 37.36, 37.50, 42.79, 56.61, 108.71, 110.78, 119.97, 126.00, 133.68, 133.93, 140.95, 156.27, 156.52.

$t_R$ 2.03 min, MS (ESI) m/z 442 [M+H] (100%)

3-(benzylamino)-4-(cyclohexylamino)-N-methylbenzenesulfonamide (47)

Following general procedure D, using 3-amino-4-(cyclohexylamino)-N-methylbenzenesulfonamide (0.170 g, 0.600 mmol) and benzylbromide (0.072 ml, 0.600 mmol). The residue was purified by flash-column chromatography (30% ethyl acetate in heptane) on silica gel to afford the desired 3-(benzylamino)-4-(cyclohexylamino)-N-methylbenzenesulfonamide (0.05 g, 0.134 mmol). (Yield: 22.3%)

$^1$H NMR (400 MHz, DMSO-d$_6$) δ 1.16-1.28 (m, 3H), 1.32-1.44 (m, 2H), 1.60-1.68 (m, 1H), 1.71-1.80 (m, 2H), 1.95-2.05 (m, 2H), 2.17 (d, J=5.16 Hz, 3H), 3.34 (s, 1H), 4.28-4.34 (m, 2H), 5.12 (d, J=6.84 Hz, 1H), 5.66 (t, J=5.28

Hz, 1H), 6.55 (d, J=8.43 Hz, 1H), 6.70 (d, J=2.09 Hz, 1H), 6.79 (q, J=5.11 Hz, 1H), 6.95 (dd, J=2.08, 8.34 Hz, 1H), 7.22-7.27 (m, 1H), 7.31-7.40 (m, 4H). $^{13}$C NMR (101 MHz, MeOD) δ 24.67, 24.86, 25.36, 25.67, 27.83, 32.71, 33.36, 51.41, 108.23, 109.51, 118.54, 124.48, 126.61, 127.21, 128.09, 134.97, 139.36, 139.90.

$t_R$ 2.12 min, MS (ESI) m/z 374 [M+H] (100%)

4-(cyclohexylamino)-N-methyl-3-((pyridin-4-ylmethyl)amino)benzenesulfonamide (48)

Following general procedure D, using 3-amino-4-(cyclohexylamino)-N-methylbenzenesulfonamide (0.150 g, 0.614 mmol) and 4-(bromomethyl)pyridinehydrobromide (0.268 g, 1.059 mmol). The residue was purified by flash-column chromatography (100% ethyl acetate) on silica gel to afford the 4-(cyclohexylamino)-N-methyl-3-((pyridin-4-ylmethyl)amino)benzenesulfonamide (0.06 g, 0.160 mmol). (Yield: 30.3%)

$^1$H NMR (400 MHz, DMSO-d$_6$) δ 1.16-1.31 (m, 3H), 1.32-1.45 (m, 2H), 1.60-1.68 (m, 1H), 1.71-1.80 (m, 2H), 1.96-2.05 (m, 2H), 2.14 (d, J=5.25 Hz, 3H), 3.31 (d, J=0.80 Hz, 1H), 4.38 (d, J=5.33 Hz, 2H), 5.10 (d, J=7.15 Hz, 1H), 5.80 (t, J=5.71 Hz, 1H), 6.55-6.61 (m, 2H), 6.79 (q, J=5.11 Hz, 1H), 6.97 (dd, J=2.02, 8.34 Hz, 1H), 7.32-7.38 (m, 2H), 8.45-8.54 (m, 2H). $^{13}$C NMR (101 MHz, MeOD) δ 24.83, 25.67, 27.72, 32.74, 46.16, 51.40, 108.40, 109.21, 118.93, 122.68, 124.58, 134.25, 139.89, 148.63, 150.71.

$t_R$ 1.47 min, MS (ESI) m/z 375 [M+H] (100%)

4-(adamantan-2-ylamino)-3-(benzylamino)-N-methylbenzenesulfonamide (49)

Following general procedure D, using 4-(adamantan-2-ylamino)-3-amino-N-methylbenzenesulfonamide (0.200 g, 0.596 mmol) and benzylbromide (0.071 ml, 0.596 mmol). The residue was purified by flash-column chromatography (30% ethyl acetate in heptane) on silica gel to afford the desired 4-(adamantan-2-ylamino)-3-(benzylamino)-N-methylbenzenesulfonamide (0.096 g, 0.226 mmol). (Yield: 37.9%)

$^1$H NMR (400 MHz, DMSO-d$_6$) δ 1.49-1.57 (m, 2H), 1.66-1.76 (m, 3H), 1.81-1.93 (m, 6H), 1.99-2.06 (m, 2H), 2.08-2.16 (m, 4H), 3.63 (s, 1H), 4.36 (s, 2H), 4.97 (s, 1H), 5.97 (s, 1H), 6.52 (d, J=8.41 Hz, 1H), 6.73 (d, J=2.11 Hz, 1H), 6.79 (q, J=5.10 Hz, 1H), 6.97 (dd, J=2.09, 8.39 Hz, 1H), 7.19-7.26 (m, 1H), 7.30-7.36 (m, 2H), 7.36-7.41 (m, 2H). $^{13}$C NMR (101 MHz, DMSO-d$_6$) δ 27.29, 27.46, 28.92, 31.25, 31.54, 37.19, 37.66, 47.24, 56.60, 108.55, 109.05, 118.02, 125.81, 127.16, 127.58, 128.76, 135.14, 139.25, 140.15.

$t_R$ 2.41 min, MS (ESI) m/z 426 [M+H] (100%)

4-(adamantan-2-ylamino)-N-methyl-3-((pyridin-4-ylmethyl)amino)benzenesulfonamide (50)

Following general procedure D, using 4-(adamantan-2-ylamino)-3-amino-N-methylbenzenesulfonamide (0,150 g, 0.447 mmol) and 4-(bromomethyl)pyridinehydrobromide (0.170 g, 0.671 mmol). The residue was purified by flash-column chromatography (100% ethyl acetate) on silica gel to afford the 4-(adamantan-2-ylamino)-N-methyl-3-((pyridin-4-ylmethyl)amino)benzenesulfonamide (0.043 g, 0,101 mmol). (Yield: 22.5%)

$^1$H NMR (400 MHz, DMSO-d$_6$) δ 1.50-1.59 (m, 2H), 1.71-1.77 (m, 2H), 1.82-1.92 (m, 6H), 2.02-2.06 (m, 2H), 2.08-2.16 (m, 5H), 3.65 (dd, J=3.03, 6.04 Hz, 1H), 4.41 (d, J=5.39 Hz, 2H), 4.95 (d, J=5.92 Hz, 1H), 6.07 (t, J=5.76 Hz, 1H), 6.54 (d, J=8.41 Hz, 1H), 6.60 (d, J=2.07 Hz, 1H), 6.80 (q, J=5.10 Hz, 1H), 6.98 (dd, J=2.05, 8.31 Hz, 1H), 7.32-7.41 (m, 2H), 8.45-8.56 (m, 2H). $^{13}$C NMR (101 MHz, DMSO-d$_6$) δ 27.28, 27.44, 28.92, 31.26, 31.53, 37.17, 37.66, 46.18, 56.60, 106.02, 108.72, 118.27, 122.70, 124.49, 125.80, 134.73, 139.26, 147.14, 149.92.

$t_R$ 1.67 min, MS (ESI) m/z 427 [M+H] (100%)

3-(benzylamino)-N-(tert-butyl)-4-(cyclohexylamino)benzenesulfonamide (51)

Following general procedure D, using 3-amino-N-(tert-butyl)-4-(cyclohexylamino)benzenesulfonamide (0.200 g, 0.614 mmol) and benzylbromide (0.073 ml, 0.614 mmol). The residue was purified by flash-column chromatography (25% ethyl acetate in heptane) on silica gel to afford the desired 3-(benzylamino)-N-(tert-butyl)-4-(cyclohexylamino)benzenesulfonamide (0.211 g, 0.508 mmol). (Yield: 83.0%)

$^1$H NMR (400 MHz, DMSO-d$_6$) δ 0.93 (s, 9H), 1.15-1.29 (m, 3H), 1.30-1.45 (m, 2H), 1.60-1.70 (m, 1H), 1.70-1.79 (m, 2H), 1.95-2.04 (m, 2H), 3.31 (s, 1H), 4.33 (d, J=5.41 Hz, 2H), 5.04 (d, J=7.18 Hz, 1H), 5.63 (t, J=5.73 Hz, 1H), 6.52 (d, J=8.45 Hz, 1H), 6.77 (d, J=2.11 Hz, 1H), 6.84 (s, 1H), 6.99 (dd, J=2.09, 8.31 Hz, 1H), 7.17-7.26 (m, 1H), 7.28-7.40 (m, 4H). $^{13}$C NMR (101 MHz, MeOD) δ 24.87, 25.70, 28.87, 32.73, 51.47, 52.84, 108.24, 109.53, 118.28, 126.55, 126.99, 128.13, 129.69, 134.92, 139.39.

$t_R$ 2.38 min, MS (ESI) m/z 416 [M+H] (95%)

N-(tert-butyl)-4-(cyclohexylamino)-3-((pyridin-4-ylmethyl)amino)benzenesulfonamide (52)

Following general procedure D, using 3-amino-N-(tert-butyl)-4-(cyclohexylamino)benzenesulfonamide (0.150 g, 0,461 mmol) and 4-(bromomethyl)pyridinehydrobromide (0.233 g, 0.922 mmol). The residue was purified by flash-column chromatography (100% ethyl acetate) on silica gel to afford the N-(tert-butyl)-4-(cyclohexylamino)-3-((pyridin-4-ylmethyl)amino)benzenesulfonamide (0.073 g, 0.175 mmol). (Yield: 38.0%)

$^1$H NMR (400 MHz, DMSO-d$_6$) δ 0.87 (s, 9H), 1.19-1.31 (m, 3H), 1.33-1.46 (m, 2H), 1.60-1.69 (m, 1H), 1.72-1.80 (m, 2H), 1.97-2.06 (m, 2H), 3.31 (s, 1H), 4.39 (d, J=5.53 Hz, 2H), 5.03 (d, J=7.14 Hz, 1H), 5.79 (t, J=5.76 Hz, 1H), 6.55 (d, J=8.46 Hz, 1H), 6.62 (d, J=2.10 Hz, 1H), 6.83 (s, 1H), 7.00 (dd, J=2.07, 8.32 Hz, 1H), 7.27-7.34 (m, 2H), 8.44-8.51 (m, 2H). $^{13}$C NMR (101 MHz, MeOD) δ 24.86, 25.71, 28.87, 28.90, 32.77, 51.47, 52.77, 108.42, 109.25, 118.61, 122.60, 129.77, 134.04, 139.49, 148.63, 150.79.

$t_R$ 1.62 min, MS (ESI) m/z 417 [M+H] (100%)

4-(adamantan-2-ylamino)-3-(benzylamino)-N-(tert-butyl)benzenesulfonamide (53)

Following general procedure D, using 4-(adamantan-2-ylamino)-3-amino-N-(tert-butyl)benzenesulfonamide (0.150 g, 0.397 mmol) and benzylbromide (0.048 ml, 0.397 mmol). The residue was purified by flash-column chromatography (25% ethyl acetate in heptane) on silica gel to afford the desired 4-(adamantan-2-ylamino)-3-(benzylamino)-N-(tert-butyl)benzenesulfonamide (0.09 g, 0.192 mmol). (Yield: 48.4%)

$^1$H NMR (400 MHz, DMSO-d$_6$) δ 0.91 (s, 9H), 1.48-1.58 (m, 2H), 1.72-1.76 (m, 2H), 1.80-1.90 (m, 6H), 2.02 (d, J=3.67 Hz, 2H), 2.12 (d, J=12.73 Hz, 2H), 3.62 (d, J=4.45

Hz, 1H), 4.31-4.41 (m, 2H), 4.89 (d, J=5.77 Hz, 1H), 5.92 (s, 1H), 6.48 (d, J=8.46 Hz, 1H), 6.78 (d, J=2.16 Hz, 1H), 6.85 (s, 1H), 7.00 (dd, J=2.10, 8.36 Hz, 1H), 7.17-7.25 (m, 1H), 7.29-7.39 (m, 4H). $^{13}$C NMR (101 MHz, MeOD) δ 27.48, 27.63, 28.88, 31.24, 31.50, 36.99, 37.42, 52.86, 56.71, 108.49, 110.92, 118.93, 126.52, 126.90, 128.13, 129.85, 135.01, 139.54, 140.33.

$t_R$ 2.61 min, MS (ESI) m/z 468 [M+H] (100%)

4-(adamantan-2-ylamino)-N-(tert-butyl)-3-((pyridin-4-ylmethyl)amino)benzenesulfonamide (54)

Following general procedure D, using 4-(adamantan-2-ylamino)-3-amino-N-(tert-butyl)benzenesulfonamide (0.150 g, 0,397 mmol) and 4-(bromomethyl)pyridinehydrobromide (0.151 g, 0.596 mmol). The residue was purified by flash-column chromatography (100% ethyl acetate) on silica gel to afford the 4-(adamantan-2-ylamino)-N-(tert-butyl)-3-((pyridin-4-ylmethyl)amino)benzenesulfonamide (0.04 g, 0.085 mmol). (Yield: 21.5%)

$^1$H NMR (400 MHz, DMSO-$d_6$) δ 0.86 (s, 9H), 1.54 (d, J=12.17 Hz, 2H), 1.75 (d, J=2.84 Hz, 2H), 1.81-1.92 (m, 6H), 2.03 (d, J=3.72 Hz, 2H), 2.13 (d, J=12.73 Hz, 2H), 3.64 (s, 1H), 4.41 (d, J=5.56 Hz, 2H), 4.88 (d, J=5.89 Hz, 1H), 6.04 (t, J=5.74 Hz, 1H), 6.51 (d, J=8.48 Hz, 1H), 6.65 (d, J=2.10 Hz, 1H), 6.85 (s, 1H), 7.01 (dd, J=2.09, 8.38 Hz, 1H), 7.28-7.35 (m, 2H), 8.45-8.50 (m, 2H). $^{13}$C NMR (101 MHz, MeOD) δ 27.49, 27.62, 28.85, 31.25, 31.51, 36.98, 37.41, 46.11, 52.77, 56.73, 108.63, 110.28, 119.09, 122.59, 129.96, 134.14, 140.10, 148.62, 150.88.

$t_R$ 1.85 min, MS (ESI) m/z 469 [M+H] (100%)

3-(benzylamino)-N-(2-(tert-butoxy)ethyl)-4-(cyclohexylamino)benzenesulfonamide (55)

Following general procedure D, using 3-amino-N-(2-(tert-butoxy)ethyl)-4-(cyclohexylamino)benzenesulfonamide (0.200 g, 0,541 mmol) to afford the desired 3-(benzylamino)-N-(2-(tert-butoxy)ethyl)-4-(cyclohexylamino)benzenesulfonamide (0.110 g, 0.239 mmol). (Yield: 44.2%)

$^1$H NMR (400 MHz, DMSO-$d_6$) δ 1.06 (s, 9H), 1.15-1.28 (m, 4H), 1.32-1.43 (m, 2H), 1.60-1.67 (m, 1H), 1.71-1.79 (m, 2H), 1.94-2.03 (m, 2H), 2.56 (q, J=6.41 Hz, 2H), 3.15 (t, J=6.38 Hz, 2H), 4.31 (d, J=5.36 Hz, 2H), 5.11 (d, J=7.23 Hz, 1H), 5.65 (t, J=5.52 Hz, 1H), 6.54 (d, J=8.45 Hz, 1H), 6.72 (d, J=2.08 Hz, 1H), 6.88 (t, J=6.12 Hz, 1H), 6.96 (dd, J=2.08, 8.28 Hz, 1H), 7.22-7.27 (m, 1H), 7.31-7.40 (m, 4H). $^{13}$C NMR (101 MHz, MeOD) δ 21.50, 24.85, 25.68, 26.34, 32.69, 43.20, 51.40, 60.15, 72.94, 108.32, 109.28, 118.35, 125.99, 126.64, 127.21, 128.12, 135.04, 139.40, 139.88.

$t_R$ 2.68 min, MS (ESI) m/z 460 [M+H] (100%)

N2-benzyl-N1-cyclohexyl-4-((4-methylpiperazin-1-yl)sulfonyl)benzene-1,2-diamine (56)

Following general procedure D, using N1-cyclohexyl-4-((4-methylpiperazin-1-yl)sulfonyl)benzene-1,2-diamine (0.200 g, 0.567 mmol) to afford the desired N2-benzyl-N1-cyclohexyl-4-((4-methylpiperazin-1-yl)sulfonyl)benzene-1,2-diamine (0.020 g, 0.045 mmol). (Yield: 7.96%)

$^1$H NMR (400 MHz, Acetone-$d_6$) δ 1.25-1.36 (m, 4H), 1.39-1.52 (m, 2H), 1.63-1.73 (m, 1H), 1.75-1.84 (m, 2H), 2.07-2.09 (m, 1H), 2.15 (s, 3H), 2.27 (t, J=5.04 Hz, 4H), 2.53-2.67 (m, 4H), 3.39-3.52 (m, 1H), 4.44 (d, J=4.98 Hz, 2H), 4.69 (d, J=7.20 Hz, 1H), 5.03 (s, 1H), 6.72 (dd, J=0.68, 8.36 Hz, 1H), 6.75 (d, J=2.09 Hz, 1H), 7.04 (dd, J=2.09, 8.32 Hz, 1H), 7.23-7.28 (m, 1H), 7.30-7.37 (m, 2H), 7.39-7.44 (m, 2H). $^{13}$C NMR (101 MHz, Acetone-$d_6$) δ 24.82, 25.76, 32.86, 45.05, 45.85, 47.57, 51.34, 53.95, 108.16, 110.66, 119.51, 121.49, 126.83, 127.37, 128.40, 134.65, 139.55, 140.13.

$t_R$ 1.62 min, MS (ESI) m/z 443 [M+H] (100%)

N2-benzyl-N1-cyclohexyl-4-(morpholinosulfonyl)benzene-1,2-diamine (57)

Following general procedure D, using N1-cyclohexyl-4-(morpholinosulfonyl)benzene-1,2-diamine (0.200 g, 0.589 mmol) to afford the desired N2-benzyl-N1-cyclohexyl-4-(morpholinosulfonyl)benzene-1,2-diamine (0.053 g, 0.123 mmol). (Yield: 20.94%)

$^1$H NMR (400 MHz, Acetone-$d_6$) δ 1.25-1.37 (m, 5H), 1.40-1.52 (m, 2H), 1.64-1.73 (m, 1H), 1.76-1.86 (m, 2H), 2.48-2.55 (m, 4H), 3.42-3.49 (m, 1H), 3.50-3.55 (m, 4H), 4.46 (d, J=3.37 Hz, 2H), 4.74 (d, J=7.06 Hz, 1H), 5.11 (t, J=5.15 Hz, 1H), 6.68-6.78 (m, 2H), 7.04 (dd, J=2.11, 8.34 Hz, 1H), 7.23-7.29 (m, 1H), 7.30-7.37 (m, 2H), 7.42 (ddd, J=0.74, 1.48, 7.71 Hz, 2H). $^{13}$C NMR (101 MHz, Acetone-$d_6$) δ 24.83, 25.76, 32.86, 46.04, 47.47, 51.36, 65.65, 108.13, 110.62, 119.60, 120.90, 126.85, 127.35, 128.43, 134.60, 139.56, 140.28.

$t_R$ 2.21 min, MS (ESI) m/z 430 [M+H] (100%)

3-(benzylamino)-4-(cyclohexylamino)-N-(2-hydroxyethyl)benzenesulfonamide (58)

To a solution of 3-(benzylamino)-N-(2-(tert-butoxy)ethyl)-4-(cyclohexylamino)benzenesulfonamide (0,110 g, 0,239 mmol) in DCM at room temperature was added phosphate (0,023 g, 0,239 mmol) dropwise. The mixture was stirred for 14 hours, and then 30 mL of water was added. The mixture was extracted with EtOAc. The combined organic phase was dried over MgSO$_4$ and concentrated in vacuo to give the desired 3-(benzylamino)-N-(2-(tert-butoxy)ethyl)-4-(cyclohexylamino)benzenesulfonamide (0.110 g, 0.239 mmol). (Yield: 50.7%)

$^1$H NMR (400 MHz, DMSO-$d_6$) δ 1.14-1.28 (m, 3H), 1.30-1.44 (m, 2H), 1.59-1.68 (m, 1H), 1.71-1.80 (m, 2H), 1.94-2.04 (m, 2H), 2.56 (t, J=6.26 Hz, 2H), 3.28 (t, J=6.74 Hz, 3H), 4.31 (d, J=5.10 Hz, 2H), 4.55 (s, 1H), 5.11 (d, J=7.24 Hz, 1H), 5.64 (t, J=5.44 Hz, 1H), 6.54 (d, J=8.48 Hz, 1H), 6.73 (d, J=2.14 Hz, 1H), 6.89 (t, J=6.06 Hz, 1H), 6.97 (dd, J=2.06, 8.35 Hz, 1H), 7.22-7.29 (m, 1H), 7.31-7.41 (m, 4H). $^{13}$C NMR (101 MHz, MeOD) δ 21.38, 24.86, 25.67, 32.70, 44.80, 51.44, 60.41, 108.28, 109.36, 118.42, 125.65, 126.65, 127.22, 128.13, 135.00, 139.32, 139.87.

$t_R$ 2.19 min, MS (ESI) m/z 404 [M+H] (90%)

2. Activity of Specific Compounds of the Invention

The IC50 values for the individual compounds of the disclosure were determined in the neuroblastoma, IMR-32 cell line. In brief, IMR-32 cells were subjected to 10 μM erastin, the latter compound is known to induce ferroptosis. A concentration gradient (ranging from 1 nM to 1 μM) of the compounds was applied to the cells. These experiments were performed in a 96-well format (in triplicate), and cell death was analyzed in a fluorescent plate reader by use of a fluorescent cell death dye (1.5 μM Sytox Green). The IC50 values depicted in Table 1 are the concentration values for the individual compounds which are able to overcome ferroptosis.

TABLE 1 structure of representative compounds of the invention.

| Compound | Structure | IUPAC name | IC$_{50}$ (nM) |
|---|---|---|---|
| 20 | 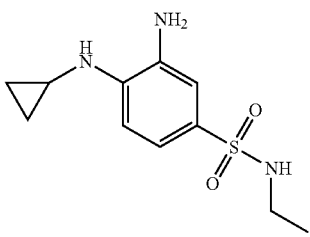 [SMILES: CCNS(=O)(=O)c1ccc(NC2CC2)c(N)c1] | 3-amino-4-(cyclopropylamino)-N-ethylbenzenesulfonamide | 76 |
| 21 | 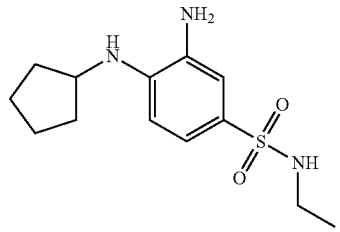 [SMILES: CCNS(=O)(=O)c1ccc(NC2CCCC2)c(N)c1] | 3-amino-4-(cyclopentylamino)-N-ethylbenzenesulfonamide | 82 |
| 22 | 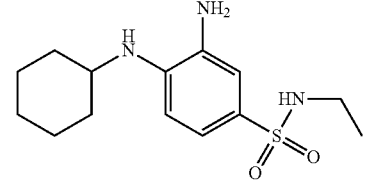 [SMILES: CCNS(=O)(=O)c1ccc(NC2CCCCC2)c(N)c1] | 3-amino-4-(cyclohexylamino)-N-ethylbenzenesulfonamide | 67 |
| 23 | 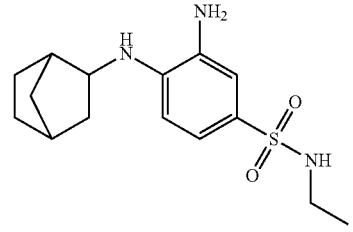 [SMILES: CCNS(=O)(=O)c1ccc(NC2CC3CCC2C3)c(N)c1] | 3-amino-4-(bicyclo[2.2.1]heptan-2-ylamino)-N-ethylbenzenesulfonamide | 28 |
| 24 | 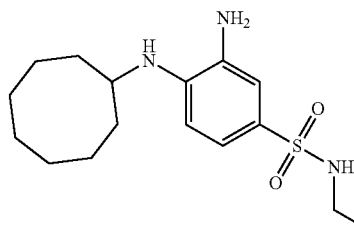 | 3-amino-4-(cyclooctylamino)-N-ethylbenzenesulfonamide | 9.3 |
| 25 | 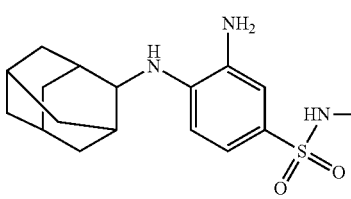 | 4-(adamantan-2-ylamino)-3-amino-N-ethylbenzenesulfonamide | 17 |

TABLE 1-continued structure of representative compounds of the invention.

| Compound | Structure | IUPAC name | IC$_{50}$ (nM) |
|---|---|---|---|
| 26 | 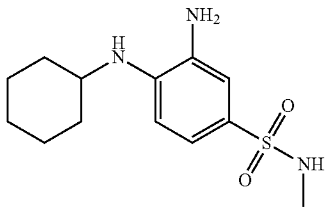 [SMILES: CNS(=O)(=O)c1ccc(NC2CCCCC2)c(N)c1] | 3-amino-4-(cyclohexylamino)-N-methylbenzenesulfonamide | 76 |
| 27 | 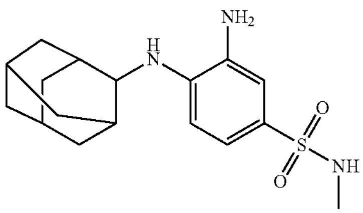 [SMILES: CNS(=O)(=O)c1ccc(NC2C3CC4CC(C3)CC2C4)c(N)c1] | 4-(adamantan-2-ylamino)-3-amino-N-methylbenzenesulfonamide | 11 |
| 28 | 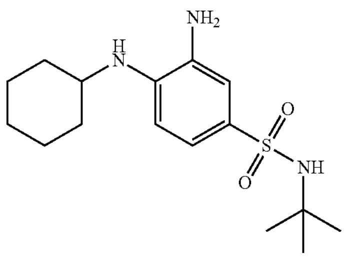 [SMILES: CC(C)(C)NS(=O)(=O)c1ccc(NC2CCCCC2)c(N)c1] | 3-amino-N-(tert-butyl)-4-(cyclohexylamino)benzenesulfonamide | 27 |
| 29 | 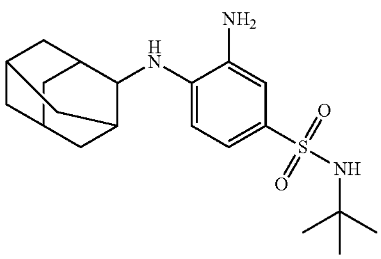 [SMILES: CC(C)(C)NS(=O)(=O)c1ccc(NC2C3CC4CC(C3)CC2C4)c(N)c1] | 4-(adamantan-2-ylamino)-3-amino-N-(tert-butyl)benzenesulfonamide | 6.0 |
| 30 | 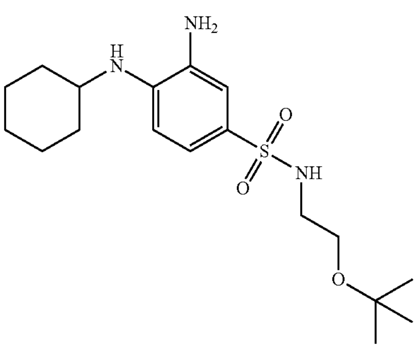 [SMILES: CC(C)(C)OCCNS(=O)(=O)c1ccc(NC2CCCCC2)c(N)c1] | 3-amino-N-(2-(tert-butoxy)ethyl)-4-(cyclohexylamino)benzenesulfonamide | 132 |
| 31 | 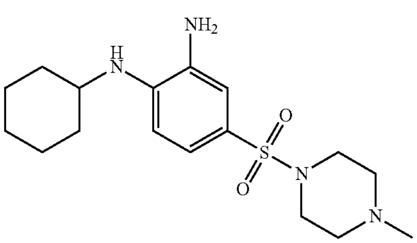 [SMILES: CN1CCN(S(=O)(=O)c2ccc(NC3CCCCC3)c(N)c2)CC1] | N1-cyclohexyl-4-((4-methylpiperazin-1-yl)sulfonyl)benzene-1,2-diamine | 206 |

TABLE 1-continued structure of representative compounds of the invention.

| Compound | Structure | IUPAC name | IC$_{50}$ (nM) |
|---|---|---|---|
| 32 | 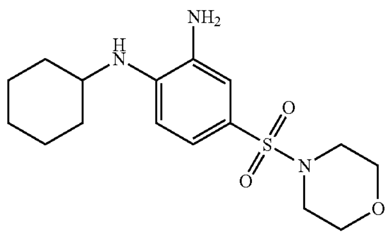 [SMILES: Nc1cc(S(=O)(=O)N2CCOCC2)ccc1NC1CCCCC1] | N1-cyclohexyl-4-(morpholinosulfonyl)benzene-1,2-diamine | 208 |
| 33 | 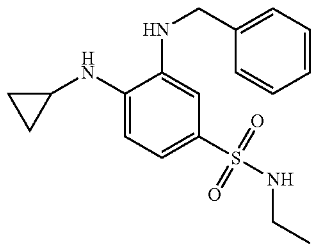 [SMILES: CCNS(=O)(=O)c1ccc(NC2CC2)c(NCc2ccccc2)c1] | 3-(benzylamino)-4-(cyclopropylamino)-N-ethylbenzenesulfonamide | 61 |
| 34 | 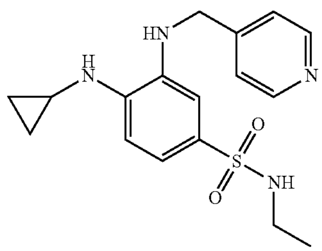 [SMILES: CCNS(=O)(=O)c1ccc(NC2CC2)c(NCc2ccncc2)c1] | 4-(cyclopropylamino)-N-ethyl-3-((pyridin-4-ylmethyl)amino)benzenesulfonamide | 128 |
| 35 | 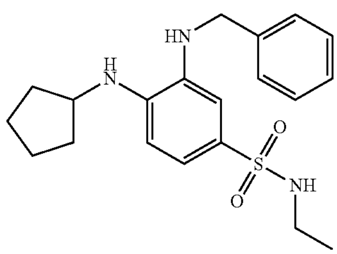 [SMILES: CCNS(=O)(=O)c1ccc(NC2CCCC2)c(NCc2ccccc2)c1] | 3-(benzylamino)-4-(cyclopentylamino)-N-ethylbenzenesulfonamide | 8.2 |
| 36 | 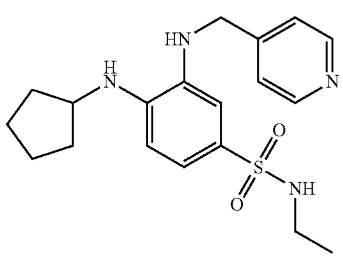 [SMILES: CCNS(=O)(=O)c1ccc(NC2CCCC2)c(NCc2ccncc2)c1] | 4-(cyclopentylamino)-N-ethyl-3-((pyridin-4-ylmethyl)amino)benzenesulfonamide | 36 |
| 37 | 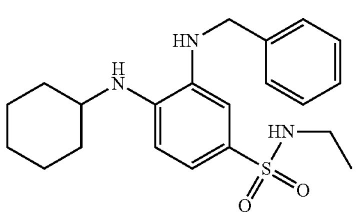 [SMILES: CCNS(=O)(=O)c1ccc(NC2CCCCC2)c(NCc2ccccc2)c1] | 3-(benzylamino)-4-(cyclohexylamino)-N-ethylbenzenesulfonamide | 4.0 |

TABLE 1-continued structure of representative compounds of the invention.

| Compound | Structure | IUPAC name | IC$_{50}$ (nM) |
|---|---|---|---|
| 38 | 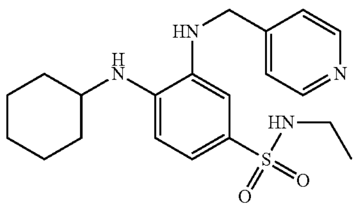 [SMILES: CCNS(=O)(=O)c1ccc(NC2CCCCC2)c(NCc2ccncc2)c1] | 4-(cyclohexylamino)-N-ethyl-3-((pyridin-4-ylmethyl)amino)benzenesulfonamide | 23 |
| 39 | 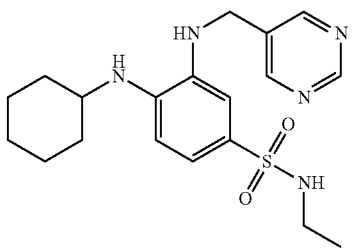 [SMILES: CCNS(=O)(=O)c1ccc(NC2CCCCC2)c(NCc2cncnc2)c1] | 4-(cyclohexylamino)-N-ethyl-3-((pyrimidin-5-ylmethyl)amino)benzenesulfonamide | 187 |
| 40 | 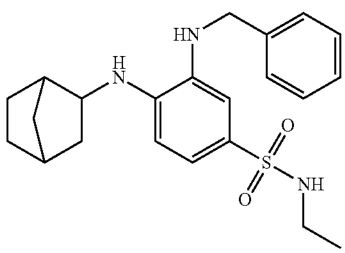 [SMILES: CCNS(=O)(=O)c1ccc(NC2CC3CCC2C3)c(NCc2ccccc2)c1] | 3-(benzylamino)-4-(bicyclo[2.2.1]heptan-2-ylamino)-N-ethylbenzenesulfonamide | 3.0 |
| 41 | 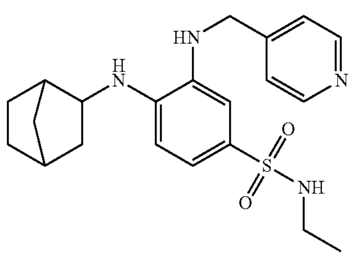 [SMILES: CCNS(=O)(=O)c1ccc(NC2CC3CCC2C3)c(NCc2ccncc2)c1] | 4-(bicyclo[2.2.1]heptan-2-ylamino)-N-ethyl-3-((pyridin-4-ylmethyl)amino)benzenesulfonamide | 9.4 |
| 42 | 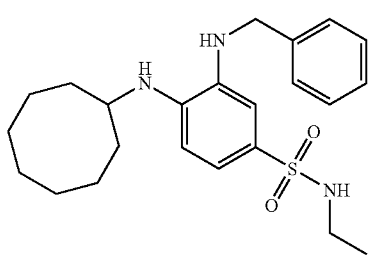 [SMILES: CCNS(=O)(=O)c1ccc(NC2CCCCCCC2)c(NCc2ccccc2)c1] | 3-(benzylamino)-4-(cyclooctylamino)-N-ethylbenzenesulfonamide | 2.4 |
| 43 | 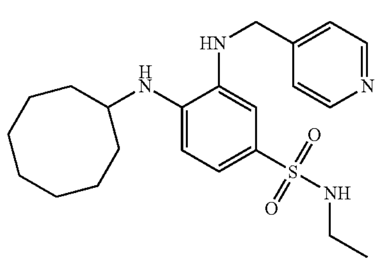 [SMILES: CCNS(=O)(=O)c1ccc(NC2CCCCCCC2)c(NCc2ccncc2)c1] | 4-(cyclooctylamino)-N-ethyl-3-((pyridin-4-ylmethyl)amino)benzenesulfonamide | 22 |

TABLE 1-continued structure of representative compounds of the invention.

| Compound | Structure | IUPAC name | IC$_{50}$ (nM) |
|---|---|---|---|
| 44 | 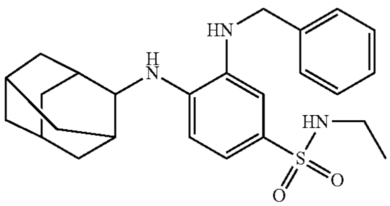 [SMILES: CCNS(=O)(=O)c1ccc(NC2C3CC4CC(C3)CC2C4)c(NCc2ccccc2)c1] | 4-(adamantan-2-ylamino)-3-(benzylamino)-N-ethylbenzenesulfonamide | 3.5 |
| 45 | 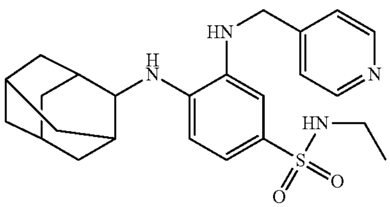 [SMILES: CCNS(=O)(=O)c1ccc(NC2C3CC4CC(C3)CC2C4)c(NCc2ccncc2)c1] | 4-(adamantan-2-ylamino)-N-ethyl-3-((pyridin-4-ylmethyl)amino)benzenesulfonamide | 3.9 |
| 46 | 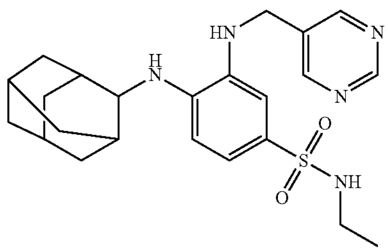 [SMILES: CCNS(=O)(=O)c1ccc(NC2C3CC4CC(C3)CC2C4)c(NCc2cncnc2)c1] | 4-(adamantan-2-ylamino)-N-ethyl-3-((pyrimidin-5-ylmethyl)amino)benzenesulfonamide | 47 |
| 47 | 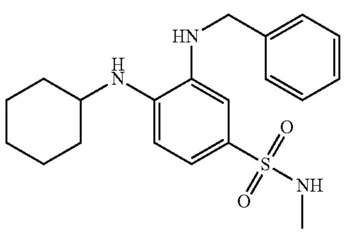 [SMILES: CNS(=O)(=O)c1ccc(NC2CCCCC2)c(NCc2ccccc2)c1] | 3-(benzylamino)-4-(cyclohexylamino)-N-methylbenzenesulfonamide | 3.7 |
| 48 | 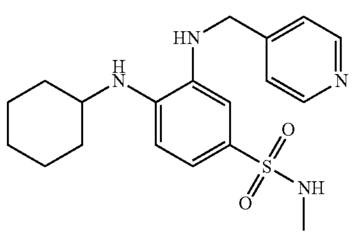 [SMILES: CNS(=O)(=O)c1ccc(NC2CCCCC2)c(NCc2ccncc2)c1] | 4-(cyclohexylamino)-N-methyl-3-((pyridin-4-ylmethyl)amino)benzenesulfonamide | 15 |
| 49 | 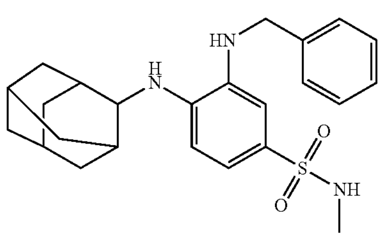 [SMILES: CNS(=O)(=O)c1ccc(NC2C3CC4CC(C3)CC2C4)c(NCc2ccccc2)c1] | 4-(adamantan-2-ylamino)-3-(benzylamino)-N-methylbenzenesulfonamide | 4.9 |

TABLE 1-continued structure of representative compounds of the invention.

| Compound | Structure | IUPAC name | IC$_{50}$ (nM) |
|---|---|---|---|
| 50 | 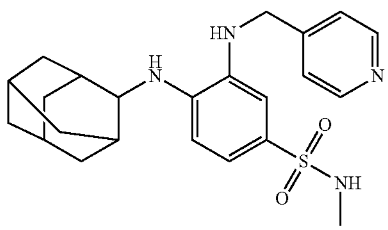 [SMILES: CNS(=O)(=O)c1ccc(NC2C3CC4CC(C3)CC2C4)c(NCc2ccncc2)c1] | 4-(adamantan-2-ylamino)-N-methyl-3-((pyridin-4-ylmethyl)amino)benzenesulfonamide | 6.4 |
| 51 | 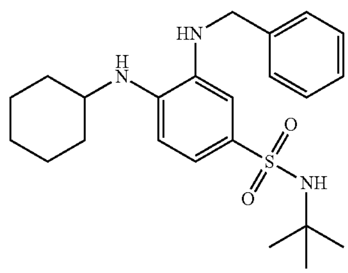 [SMILES: CC(C)(C)NS(=O)(=O)c1ccc(NC2CCCCC2)c(NCc2ccccc2)c1] | 3-(benzylamino)-N-(tert-butyl)-4-(cyclohexylamino)benzenesulfonamide | 6.2 |
| 52 | 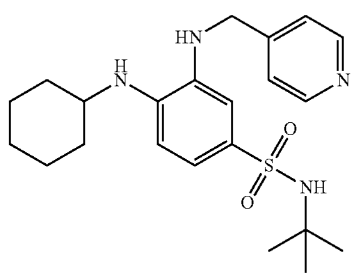 [SMILES: CC(C)(C)NS(=O)(=O)c1ccc(NC2CCCCC2)c(NCc2ccncc2)c1] | N-(tert-butyl)-4-(cyclohexylamino)-3-((pyridin-4-ylmethyl)amino)benzenesulfonamide | 11 |
| 53 | 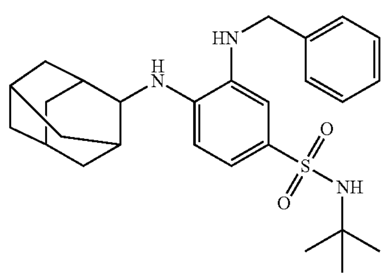 [SMILES: CC(C)(C)NS(=O)(=O)c1ccc(NC2C3CC4CC(C3)CC2C4)c(NCc2ccccc2)c1] | 4-(adamantan-2-ylamino)-3-(benzylamino)-N-(tert-butyl)benzenesulfonamide | 3.4 |
| 54 | 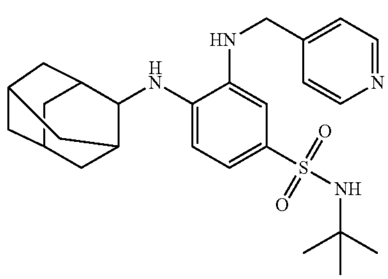 [SMILES: CC(C)(C)NS(=O)(=O)c1ccc(NC2C3CC4CC(C3)CC2C4)c(NCc2ccncc2)c1] | 4-(adamantan-2-ylamino)-N-(tert-butyl)3-((pyridin-4-ylmethyl)amino)benzenesulfonamide | 5.2 |

TABLE 1-continued structure of representative compounds of the invention.

| Compound | Structure | IUPAC name | IC$_{50}$ (nM) |
|---|---|---|---|
| 55 | 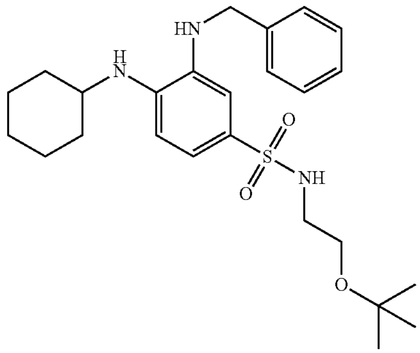 [SMILES: CC(C)(C)OCCNS(=O)(=O)c1ccc(NC2CCCCC2)c(NCc2ccccc2)c1] | 3-(benzylamino)-N-(2-(tert-butoxy)ethyl)-4-(cyclohexylamino)benzenesulfonamide | 22 |
| 56 | 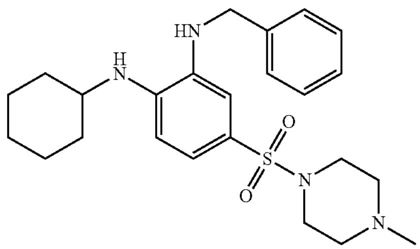 [SMILES: CN1CCN(S(=O)(=O)c2ccc(NC3CCCCC3)c(NCc3ccccc3)c2)CC1] | N2-benzyl-N1-cyclohexyl-4-((4-methylpiperazin-1-yl)sulfonyl)benzene-1,2-diamine | 33 |
| 57 | 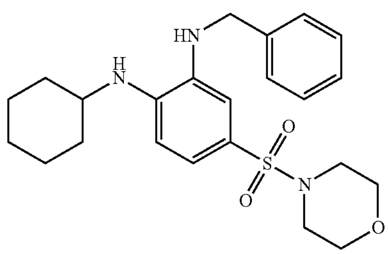 [SMILES: O=S(=O)(c1ccc(NC2CCCCC2)c(NCc2ccccc2)c1)N1CCOCC1] | N2-benzyl-N1-cyclohexyl-4-(morpholinosulfonyl)benzene-1,2-diamine | 30 |
| 58 | 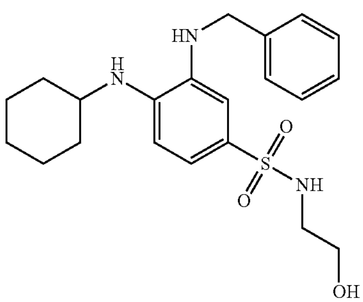 [SMILES: O=S(=O)(NCCO)c1ccc(NC2CCCCC2)c(NCc2ccccc2)c1] | 3-(benzylamino)-4-(cyclohexylamino)-N-(2-hydroxyethyl)benzenesulfonamide | 14 |

The last column depicts the IC50 values for inhibiting ferroptosis in the IMR-32 neuroblastoma cell line stimulated with 10 μM erastin.

3. Pharmacokinetic Analysis of Representative Compounds

In a next step a subset of compounds was subjected to ADME analysis. Thereto the metabolism by murine and human microsomes of representative compounds of the disclosure was measured. The compound ferrostatin-1 (Fer-1, described in S. J. Dixon et al. (2012) *Cell* 149, 1060-1072), originally described to inhibit ferroptosis, was used a control. In addition, the plasma stability in murine and human plasma was measured. The percentage of remaining compounds was measured by LC-MS. A compilation of the ADME data is represented in Table 2.

TABLE 2 in vitro ADME of selected compounds

| Compound | Solubility $^a$(μM) | Microsomal stability Half-life (t$_{1/2}$) (min)$^b$ | | Plasma stability % recovery after 6 h$^c$ | |
|---|---|---|---|---|---|
| | | Human | Mouse | Human | Mouse |
| Fer-1 | >200 | 6.9 ± 0.2 | 1.9 ± 0.6 | 100 | 0 |
| 22 | 12.5-25 | 37 ± 3 | 31 ± 5 | 81.9 | 86.2 |
| 31 | >200 | n.d. | n.d | n.d | n.d |
| 32 | >200 | n.d | n.d | n.d | n.d |

TABLE 2-continued in vitro ADME of selected compounds

| Compound | Solubility $^a$(μM) | Microsomal stability Half-life ($t_{1/2}$) (min)$^b$ | | Plasma stability % recovery after 6 h$^c$ | |
|---|---|---|---|---|---|
| | | Human | Mouse | Human | Mouse |
| 37 | 12.5-25 | 88 ± 16 | 187 ± 41 | 100 | 98.6 |
| 39 | 100-200 | n.d | n.d | n.d | n.d |
| 44 | 12.5-25 | 36 ± 11 | 31 ± 6 | 100 | 99.4 |
| 45 | 12.5-25 | 64 ± 10 | 26 ± 5 | 100 | 100 |
| 56 | 25-50 | n.d | n.d | n.d | n.d |
| 57 | 25-50 | n.d | n.d | n.d | n.d |
| 58 | 100-200 | n.d | n.d | n.d | n.d |

$^a$Final test compound concentration range of between 3.125 μM and 200 μM [4 μM DMSO solution in 196 μM buffer solution (10 mM PBS pH 7.4)]
$^b$Metabolism by microsomes (CYP450 and other NADPH-dependent enzymes) was monitored and expressed as half-life (min)
$^c$Percentage of remaining parent compound
n.d. = not determined 4. In Vivo Use of Representative Compounds To determine the stability of lead ferrostatin analogues in vivo, blood is sampled in function of time upon ip or iv injection of the leads and their concentration will be measured using HPLC. Next, based on these pharmacokinetic data the most stable compounds of the disclosure are tested in ferroptosis-driven liver damage. In particular, ferroptotic hepatotoxicity is induced by diquat (M. Higuchi et al. (2011) *Biometals* 24(6): 1123-31, ML162 (W. S. Yang et al. (2014) *Cell* 156 (1-2): 317-31), piperazine-Erastin (W. S. Yang et al. (2014) *Cell* 156 (1-2): 317-31) or acetaminophen (R. P. van Swelm et al. (2012) *Toxicol. Sci.* 129(1): 225-33). To illustrate their specificity, the compounds are also tested in necroptotic liver damage induced by concanavalin A (Y. Zhou et al. (2013) *Mediators Inflamm.* 2013: 706156) and apoptotic liver damage induced by TNF/Galactosamine (J. Liu et al. (2013) *Oxid. Med. Cell Longev.* 2013: 305861). Liver damage is monitored by analyzing aspartate transaminase (AST) and alanine transaminase (ALT) levels in blood samples, but also cytosolic lactate dehydrogenase, mitochondrial DNA and lysosomal hexoaminidase as markers of cell death. This chemical-induced liver damage approach allows us to pinpoint quickly the most promising lead ferrostatin analogue. In a parallel genetic approach, we want to use tamoxifen-inducible GPX4 deficient mice that develop ferroptosis-driven acute renal failure (Angeli J. P. Friedmann et al. (2014) *Nat Cell Biol.* 16(12):1180-91) to validate lead ferrostatin analogues. The most effective compound is subsequently validated in ischemia-reperfusion related pathologies such as cerebral or cardiac infarction, kidney IR and different models of septic shock (TNF-, LPS- and cecal ligation and puncture-induced shock; expertize in house). In addition, we are analyzing the role of iron-catalyzed necrosis in a clinical relevant setting vis-a-vis iron-storage disorders. Therefore, we are studying the role of iron-catalyzed necrosis in primary skin fibroblasts derived from patients with specific iron-storage disorders. We focus on cells derived from Friedreich ataxia patients with defects in the frataxin (FXN) gene because these cells were previously shown to be more sensitive for iron-catalyzed oxidative stress-induced cell death (A. Wong et al. (1999) *Hum Mol. Genet.* 8(3):425-30).

The invention claimed is:
1. A compound of formula (I)

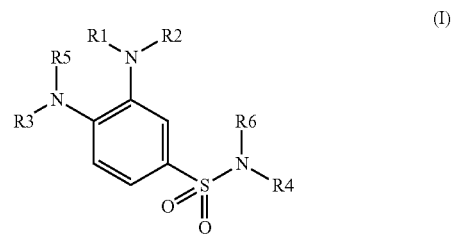

(I)

wherein
R1 is selected from the group consisting of H, C1-C4-alkyl aryl, C1-C4-alkyl pyridine, C1-C4-alkyl pyrimidine, C1-C4-alkyl pyrazine, and C1-C4-alkyl pyridazine;
R2 is selected from the group consisting of H, C1-C4-alkyl aryl, C1-C4-alkyl pyridine, C1-C4-alkyl pyrimidine, C1-C4-alkyl pyrazine, and C1-C4-alkyl pyridazine;
R3 is a C3-C12-cycloalkyl, optionally substituted with one or more halogens, optionally replacing one or more carbons by heteroatoms in the cycloalkyl ring structure;
R4 is a C1-C4-alkyl, wherein said C1-C4 alkyl is optionally terminated with an XR7 group, wherein X is a heteroatom and R7 is H or C1-C4 alkyl;
R5 is selected from the group consisting of H and C3-C12-cycloalkyl, optionally substituted with one or more halogens, optionally replacing one or more carbons by heteroatoms in the cycloalkyl ring structure;
R6 is selected from the group consisting of H and a C1-C4-alkyl, wherein in said C1-C4 alkyl, the carbon atoms are optionally replaced by one or more heteroatoms; and
R4 and R6 can form a C2-C6 cycloalkyl ring structure optionally in said ring structure one or more carbons are replaced by heteroatoms and said ring structure can be substituted by one or more halogens; and
a salt, a stereoisomer, a tautomer, an N-oxide, a hydrate, or a solvate thereof, and individual enantiomers and diastereomers thereof.
2. A compound according to claim 1 selected from the group consisting of:
3-amino-4-(cyclopropylamino)-N-ethylbenzenesulfonamide,
3-amino-4-(cyclopentylamino)-N-ethylbenzenesulfonamide,
3-amino-4-(cyclohexylamino)-N-ethylbenzenesulfonamide,
3-amino-4-(bicyclo[2.2.1]heptan-2-ylamino)-N-ethylbenzenesulfonamide,
3-amino-4-(cyclooctylamino)-N-ethylbenzenesulfonamide,
4-(adamantan-2-ylamino)-3-amino-N-ethylbenzenesulfonamide,
3-amino-4-(cyclohexylamino)-N-methylbenzenesulfonamide,
4-(adamantan-2-ylamino)-3-amino-N-methylbenzenesulfonamide,
3-amino-N-(tert-butyl)-4-(cyclohexylamino)benzenesulfonamide,
4-(adamantan-2-ylamino)-3-amino-N-(tert-butyl)benzenesulfonamide, 3-amino-N-(2-(tert-butoxy)ethyl)-4-(cyclohexylamino) benzenesulfonamide, N1-cyclohexyl-4-((4-methylpiperazin-1-yl)sulfonyl)benzene-1,2-diamine, N1-cyclohexyl-4-(morpholinosulfonyl)benzene-1,2-diamine, 3-(benzylamino)-4-(cyclopropylamino)-N-ethylbenzenesulfonamide, 4-(cyclopropylamino)-N-ethyl-3-((pyridin-4-ylmethyl)amino)benzenesulfonamide, 3-(benzylamino)-4-(cyclopentylamino)-N-ethylbenzenesulfonamide, 4-(cyclopentylamino)-N-ethyl-3-((pyridin-4-ylmethyl)amino)benzenesulfonamide, 3-(benzylamino)-4-(cyclohexylamino)-N-ethylbenzenesulfonamide, 4-(cyclohexylamino)-N-ethyl-3-((pyridin-4-ylmethyl)amino)benzenesulfonamide, 4-(cyclohexylamino)-N-ethyl-3-((pyrimidin-5-ylmethyl)amino)benzenesulfonamide, 3-(benzylamino)-4-(bicyclo[2.2.1]heptan-2-ylamino)-N-ethylbenzenesulfonamide, 4-(bicyclo[2.2.1]heptan-2-ylamino)-N-ethyl-3-((pyridin-4-ylmethyl)amino)benzenesulfonamide, 3-(benzylamino)-4-(cyclooctylamino)-N-ethylbenzenesulfonamide, 4-(cyclooctylamino)-N-ethyl-3-((pyridin-4-ylmethyl)amino)benzenesulfonamide, 4-(adamantan-2-ylamino)-3-(benzylamino)-N-ethylbenzenesulfonamide, 4-(adamantan-2-ylamino)-N-ethyl-3-((pyridin-4-ylmethyl)amino)benzenesulfonamide, 4-(adamantan-2-ylamino)-N-ethyl-3-((pyrimidin-5-ylmethyl)amino)benzenesulfonamide, 3-(benzylamino)-4-(cyclohexylamino)-N-methylbenzenesulfonamide, 4-(cyclohexylamino)-N-methyl-3-((pyridin-4-ylmethyl)amino)benzenesulfonamide, 4-(adamantan-2-ylamino)-3-(benzylamino)-N-methylbenzenesulfonamide, 4-(adamantan-2-ylamino)-N-methyl-3-((pyridin-4-ylmethyl)amino)benzenesulfonamide, 3-(benzylamino)-N-(tert-butyl)-4-(cyclohexylamino)benzenesulfonamide, N-(tert-butyl)-4-(cyclohexylamino)-3-((pyridin-4-ylmethyl)amino)benzenesulfonamide, 4-(adamantan-2-ylamino)-3-(benzylamino)-N-(tert-butyl)benzenesulfonamide, 4-(adamantan-2-ylamino)-N-(tert-butyl)-3-((pyridin-4-ylmethyl)amino)benzenesulfonamide, 3-(benzylamino)-N-(2-(tert-butoxy)ethyl)-4-(cyclohexylamino)benzenesulfonamide, N2-benzyl-N1-cyclohexyl-4-((4-methylpiperazin-1-yl)sulfonyl)benzene-1,2-diamine, N2-benzyl-N1-cyclohexyl-4-(morpholinosulfonyl)benzene-1,2-diamine, and 3-(benzylamino)-4-(cyclohexylamino)-N-(2-hydroxyethyl)benzenesulfonamide.

3. A medicament comprising:
the compound of claim 1, or a stereoisomer, a tautomer, an N-oxide, a hydrate, a solvate, or a salt thereof in an amount sufficient to inhibit ferroptosis and/or oxytosis in a subject.

4. A pharmaceutical composition comprising:
the compound of claim 1, or a stereoisomer, a tautomer, an N-oxide, a hydrate, a solvate, a salt thereof, a pharmaceutically acceptable salt thereof, or a mixture of any thereof, and
a pharmaceutically acceptable carrier or diluent.

5. A method of inhibiting ferroptosis and/or oxytosis in a subject, the method comprising:
administering to the subject the pharmaceutical composition according to claim 4 so as to inhibit ferroptosis and/or oxytosis in the subject.

6. A method of treating a subject for a disease where an excess of ferroptosis and/or oxytosis occurs wherein the disease is selected from stroke, myocardial infarction, diabetes, sepsis, transplant rejection, neurodegenerative diseases, Alzheimer's Disease, Parkinson's Disease, Amyotrophic lateral sclerosis, Huntington's Disease, Dementia with Lewy bodies, Friedreich's ataxia, and/or multiple sclerosis, the method comprising:
administering to the subject the pharmaceutical composition according to claim 4.

7. A pharmaceutical composition comprising:
the compound of claim 2, or a stereoisomer, tautomer, N-oxide, hydrate, solvate, salt, pharmaceutically acceptable salt, or mixture of any thereof, and
a pharmaceutically acceptable carrier and/or diluent.

8. A method of inhibiting ferroptosis and/or oxytosis in a subject, the method comprising:
administering to the subject the pharmaceutical composition according to claim 7 so as to inhibit ferroptosis and/or oxytosis in the subject.

9. A method of treating a subject for a disease where an excess of ferroptosis and/or oxytosis occurs wherein the disease is selected from stroke, myocardial infarction, diabetes, sepsis, transplant rejection, a neurodegenerative disease, Alzheimer's Disease, Parkinson's Disease, Amyotrophic lateral sclerosis, Huntington's Disease, Dementia with Lewy bodies, Friedreich's ataxia, and/or multiple sclerosis, the method comprising:
administering to the subject the pharmaceutical composition of claim 7.

* * * * *